(12) United States Patent
Wang et al.

(10) Patent No.: US 12,235,217 B2
(45) Date of Patent: Feb. 25, 2025

(54) DIAGNOSTIC TEST KITS FOR SAMPLE PREPARATION AND ANALYSIS

(71) Applicant: Scanwell Health, Inc., Los Angeles, CA (US)

(72) Inventors: Yunyuan Vivian Wang, Tustin, CA (US); Aaron Alexander Rowe, Toluca Lake, CA (US); Hui-Ling Koh, Santa Ana, CA (US); Stephen L. Chen, Tustin, CA (US); K C Chen, Anaheim, CA (US)

(73) Assignee: Scanwell Health, Inc., Franklin Lakes, NJ (US)

( * ) Notice: Subject to any disclaimer, the term of this patent is extended or adjusted under 35 U.S.C. 154(b) by 532 days.

(21) Appl. No.: 17/098,236

(22) Filed: Nov. 13, 2020

(65) Prior Publication Data

US 2021/0231574 A1    Jul. 29, 2021

Related U.S. Application Data

(60) Provisional application No. 62/934,655, filed on Nov. 13, 2019.

(51) Int. Cl.
    *G01N 21/78*    (2006.01)
    *G01N 1/34*    (2006.01)

(52) U.S. Cl.
    CPC ............... *G01N 21/78* (2013.01); *G01N 1/34* (2013.01)

(58) Field of Classification Search
    None
    See application file for complete search history.

(56) References Cited

U.S. PATENT DOCUMENTS 3,630,680 A * 12/1971 Rittersdorf ............. G01N 33/72
                                                       422/420
4,158,546 A *  6/1979 Lam ....................... G01N 33/72
                                                       422/424
(Continued)

FOREIGN PATENT DOCUMENTS

CN        206489079 U       9/2017
CN        307268445         4/2022
(Continued)

OTHER PUBLICATIONS

Belyakov et al., J. Colloid Interface Sci. 285: 18-26 (2005).*
(Continued)

*Primary Examiner* — Erin M. Bowers
(74) *Attorney, Agent, or Firm* — Knobbe, Martens, Olson & Bear LLP

(57) ABSTRACT

A method for analyzing a sample includes introducing the sample into a vessel including a cation-exchange resin, where the cation-exchange resin has a high affinity to one or more interferent species in the sample, directing the sample through the cation-exchange resin to thereby capture one or more interference species in the cation-exchange resin to purify the sample, and releasing the purified sample from the vessel. Additionally, a method for analyzing a sample includes receiving an image depicting a diagnostic test region and a color reference chart, converting a test region image portion of the image to an analytical color space, determining first and second coordinate values characterizing the test region image portion in the analytical color space, and providing a quantitative measurement of an analyte of interest in the sample based on the first and/or (Continued)

second coordinate values and a predictive formula based on the color reference chart.

14 Claims, 18 Drawing Sheets
(10 of 18 Drawing Sheet(s) Filed in Color)

(56) References Cited

U.S. PATENT DOCUMENTS

| | | | |
|---|---|---|---|
| 4,843,377 A | 6/1989 | Fuller et al. | |
| 4,976,923 A | 12/1990 | Lipsky et al. | |
| 5,119,830 A | 6/1992 | Davis | |
| 5,260,219 A | 11/1993 | Fritz | |
| 5,408,535 A | 4/1995 | Howard, III et al. | |
| 5,470,750 A | 11/1995 | Bar-Or | |
| 5,501,837 A | 3/1996 | Sayles | |
| 5,595,187 A | 1/1997 | Davis | |
| 5,976,469 A | 11/1999 | Davis | |
| D457,246 S | 5/2002 | Mazel et al. | |
| 6,514,461 B1 | 2/2003 | Lappe et al. | |
| 6,537,501 B1 | 3/2003 | Holl et al. | |
| 6,565,814 B1 | 5/2003 | Anraku et al. | |
| 7,097,103 B2 | 8/2006 | Tseng | |
| 7,190,818 B2 | 3/2007 | Ellis et al. | |
| 7,197,169 B2 | 3/2007 | Wang | |
| 7,267,799 B1 | 9/2007 | Borich et al. | |
| 7,292,718 B2 | 11/2007 | Douglass | |
| 7,313,257 B2 | 12/2007 | Roman | |
| 7,344,081 B2 | 3/2008 | Tseng | |
| 7,420,663 B2 | 9/2008 | Wang et al. | |
| 7,428,325 B2 | 9/2008 | Douglass et al. | |
| 7,474,390 B2 | 1/2009 | Robinson et al. | |
| 7,622,729 B2 | 11/2009 | Duesbury | |
| 7,652,268 B2 | 1/2010 | Patel | |
| D633,209 S | 2/2011 | Boessneck et al. | |
| D637,310 S | 5/2011 | Barbieux et al. | |
| 8,068,666 B2 | 11/2011 | Gregory et al. | |
| 8,073,248 B2 | 12/2011 | Brunner et al. | |
| 8,145,431 B2 | 3/2012 | Kloepfer et al. | |
| 8,150,115 B2 | 4/2012 | Capewell | |
| 8,268,636 B2 | 9/2012 | Nazareth et al. | |
| 8,506,901 B2 | 8/2013 | Chen et al. | |
| D690,828 S | 10/2013 | Yoon et al. | |
| 8,655,009 B2 | 2/2014 | Chen et al. | |
| D706,930 S | 6/2014 | Lin et al. | |
| D712,060 S | 8/2014 | Tippett et al. | |
| 8,809,066 B2 | 8/2014 | Matsumoto | |
| 8,877,140 B2 | 11/2014 | Chen et al. | |
| 8,889,424 B2 | 11/2014 | Ehrenkranz et al. | |
| 8,911,679 B2 | 12/2014 | Chen et al. | |
| 8,916,390 B2 | 12/2014 | Ozean et al. | |
| 8,976,252 B2 | 3/2015 | Koh et al. | |
| 8,998,613 B2 | 4/2015 | Jung et al. | |
| 8,999,728 B2 | 4/2015 | Nazareth et al. | |
| 9,042,630 B2 | 5/2015 | Binnig et al. | |
| 9,063,091 B2 | 6/2015 | Tsai et al. | |
| 9,230,187 B2 | 1/2016 | Hamsici et al. | |
| 9,240,039 B2 | 1/2016 | Cong et al. | |
| 9,285,323 B2 | 3/2016 | Burg et al. | |
| 9,307,214 B1 | 4/2016 | Liu et al. | |
| 9,354,181 B2 | 5/2016 | Barstis et al. | |
| 9,386,221 B2 | 7/2016 | Kauniskangas et al. | |
| 9,445,749 B2 | 9/2016 | Erickson et al. | |
| 9,466,103 B2 | 10/2016 | Athelogou et al. | |
| 9,466,104 B2 | 10/2016 | Tsai et al. | |
| 9,489,703 B2 | 11/2016 | Kauniskangas et al. | |
| 9,525,867 B2 | 12/2016 | Thomas et al. | |
| 9,532,060 B2 | 12/2016 | Mesh-Iliescu et al. | |
| 9,554,109 B2 | 1/2017 | Yao | |
| 9,569,858 B2 | 2/2017 | Babcock et al. | |
| 9,600,878 B2 | 3/2017 | Tsai et al. | |
| 9,686,540 B2 | 6/2017 | Zhou et al. | |
| 9,689,803 B1 | 6/2017 | Ruttner | |
| 9,756,324 B1 | 9/2017 | Flanagan et al. | |
| 9,778,200 B2 | 10/2017 | Tsai et al. | |
| 9,787,815 B2 | 10/2017 | Erickson et al. | |
| 9,818,193 B2 | 11/2017 | Smart | |
| 9,824,441 B2 | 11/2017 | Satish et al. | |
| 9,833,783 B1 | 12/2017 | Klein et al. | |
| 9,857,372 B1 | 1/2018 | Pulitzer et al. | |
| 9,857,373 B1 | 1/2018 | Pulitzer et al. | |
| 9,863,811 B2 | 1/2018 | Burg et al. | |
| 9,888,186 B2 | 2/2018 | Zhou et al. | |
| 9,903,857 B2 | 2/2018 | Polwart et al. | |
| D812,242 S | 3/2018 | Chang et al. | |
| 9,933,359 B2 | 4/2018 | Zehler et al. | |
| 9,978,153 B2 | 5/2018 | Kisner et al. | |
| 9,990,560 B2 | 6/2018 | Decker et al. | |
| 10,019,656 B2 | 7/2018 | Huang et al. | |
| 10,055,837 B2 | 8/2018 | Lee et al. | |
| 10,068,329 B2 | 9/2018 | Adiri et al. | |
| 10,088,411 B2 | 10/2018 | Shyam et al. | |
| 10,089,753 B1 | 10/2018 | Fegyver et al. | |
| 10,101,342 B2 | 10/2018 | Nazareth et al. | |
| 10,132,802 B2 | 11/2018 | Ehrenkranz | |
| 10,168,322 B2 | 1/2019 | Nazareth et al. | |
| 10,175,162 B2 | 1/2019 | Jia et al. | |
| 10,210,626 B2 | 2/2019 | Chiba et al. | |
| 10,267,743 B2 | 4/2019 | Burg et al. | |
| 10,331,924 B2 | 6/2019 | Pulitzer et al. | |
| 10,352,946 B2 | 7/2019 | Nazareth et al. | |
| 10,354,166 B2 | 7/2019 | Nahum et al. | |
| 10,354,412 B2 | 7/2019 | Kisner et al. | |
| D857,228 S | 8/2019 | Kaplan et al. | |
| 10,395,368 B2 | 8/2019 | Berezhna et al. | |
| 10,449,538 B1 | 10/2019 | Carrano et al. | |
| 10,473,659 B2 | 11/2019 | Pulitzer et al. | |
| 10,477,175 B2 | 11/2019 | Ogasawara et al. | |
| 10,498,936 B2 | 12/2019 | Ehrenkranz | |
| 10,527,555 B2 | 1/2020 | Pulitzer et al. | |
| 10,559,081 B2 | 2/2020 | Omer et al. | |
| 10,571,395 B2 | 2/2020 | Karlovac et al. | |
| D878,622 S | 3/2020 | Wild et al. | |
| D879,999 S | 3/2020 | Wronko | |
| 10,605,741 B2 | 3/2020 | Lu et al. | |
| 10,635,870 B2 | 4/2020 | Pulitzer et al. | |
| 10,636,527 B2 | 4/2020 | Pulitzer et al. | |
| 10,663,466 B2 | 5/2020 | Ozean et al. | |
| D886,901 S | 6/2020 | Hussey et al. | |
| 10,670,533 B2 | 6/2020 | Nazareth et al. | |
| 10,681,516 B2 | 6/2020 | Zin et al. | |
| 10,753,932 B2 | 8/2020 | Hopper | |
| 10,769,489 B2 | 9/2020 | Nahum et al. | |
| 10,796,183 B2 | 10/2020 | Topal et al. | |
| 10,835,122 B2 | 11/2020 | Pulitzer et al. | |
| 10,890,534 B2 | 1/2021 | Pulitzer et al. | |
| 10,943,368 B1 | 3/2021 | Ha | |
| 10,948,352 B2 | 3/2021 | Burg | |
| D915,618 S | 4/2021 | Heron | |
| 10,983,065 B2 | 4/2021 | Burg | |
| 10,991,096 B2 | 4/2021 | Adiri et al. | |
| 11,026,624 B2 | 6/2021 | Adiri et al. | |
| 11,030,778 B2 | 6/2021 | Burg et al. | |
| 11,087,467 B2 | 8/2021 | Adiri et al. | |
| 11,107,585 B2 | 8/2021 | Pulitzer et al. | |
| D932,046 S | 9/2021 | Jobin | |
| D932,051 S | 9/2021 | Masuda et al. | |
| 11,112,406 B2 | 9/2021 | Pulitzer et al. | |
| 11,120,235 B2 | 9/2021 | Pulitzer et al. | |
| D938,608 S | 12/2021 | Jones et al. | |
| D945,008 S | 3/2022 | Smith et al. | |
| D951,479 S | 5/2022 | Versteeg et al. | |
| D970,033 S | 11/2022 | Marcelpoil et al. | |
| D979,092 S | 2/2023 | Krayer et al. | |
| D993,444 S | 7/2023 | Masuda | |
| 11,988,596 B2 | 5/2024 | Marcelpoil et al. | |
| 11,996,183 B2 | 5/2024 | Rowe et al. | |
| 2003/0108450 A1 | 6/2003 | Mainquist et al. | |
| 2005/0221504 A1 | 10/2005 | Petruno et al. | |
| 2007/0026530 A1 | 2/2007 | Wu et al. | |
| 2007/0196862 A1 | 8/2007 | Wang | |
| 2008/0287316 A1 | 11/2008 | Spivey et al. | |
| 2012/0063652 A1 | 3/2012 | Chen et al. | |
| 2012/0106811 A1 | 5/2012 | Chen et al. | |

(56) References Cited

U.S. PATENT DOCUMENTS

| | | |
|---|---|---|
| 2013/0273666 A1 | 10/2013 | Chen et al. |
| 2014/0294265 A1 | 12/2014 | Chen et al. |
| 2015/0211987 A1 | 7/2015 | Burg et al. |
| 2015/0254844 A1 | 9/2015 | Tsai et al. |
| 2015/0325006 A1 | 11/2015 | Adiri et al. |
| 2016/0139156 A1 | 5/2016 | Lakdawala et al. |
| 2016/0222373 A1 | 8/2016 | Jia |
| 2016/0245793 A1 | 8/2016 | Samsoondar |
| 2016/0281150 A1 | 9/2016 | Rawlings et al. |
| 2016/0300420 A1 | 10/2016 | Li et al. |
| 2018/0190373 A1 | 7/2018 | Pulitzer et al. |
| 2018/0196037 A1 | 7/2018 | Polwart et al. |
| 2018/0259449 A1 | 9/2018 | Poulsen et al. |
| 2018/0364224 A1 | 12/2018 | Pulitzer et al. |
| 2018/0372717 A1 | 12/2018 | Tu et al. |
| 2019/0148014 A1 | 5/2019 | Pulitzer et al. |
| 2019/0302009 A1 | 10/2019 | Borich et al. |
| 2019/0376966 A1 | 12/2019 | Pulitzer et al. |
| 2020/0126227 A1 | 4/2020 | Adiri et al. |
| 2020/0242769 A1 | 7/2020 | Limburg et al. |
| 2020/0286600 A1 | 9/2020 | De Brouwer et al. |
| 2020/0319140 A1 | 10/2020 | Saratkar et al. |
| 2021/0016280 A1 | 1/2021 | Flesher |
| 2021/0089814 A1 | 3/2021 | Lopes et al. |
| 2021/0142890 A1 | 5/2021 | Adiri et al. |
| 2022/0084659 A1 | 3/2022 | Rowe et al. |
| 2022/0128455 A1 | 4/2022 | Marcelpoil et al. |
| 2023/0095831 A1 | 3/2023 | Ehrenkranz |
| 2023/0296600 A1 | 9/2023 | Rowe et al. |
| 2024/0116049 A1 | 4/2024 | Feichtinger et al. |

FOREIGN PATENT DOCUMENTS

| | | |
|---|---|---|
| EP | 3477270 A1 | 5/2019 |
| EP | 3581921 A1 | 12/2019 |
| EP | 3591385 A1 | 1/2020 |
| EP | 3651162 A1 | 5/2020 |
| IN | 372158 | 3/2024 |
| KR | 101492972 B1 | 2/2015 |
| RU | 2422381 * | 6/2011 |
| WO | WO 2012/131386 A1 | 10/2012 |
| WO | WO 2013/116831 A1 | 8/2013 |
| WO | WO 2014/025415 A2 | 2/2014 |
| WO | WO 2014/057159 A1 | 4/2014 |
| WO | WO 2014/178062 A2 | 11/2014 |
| WO | WO 2017/138946 A1 | 8/2017 |
| WO | WO 2017/140686 A1 | 8/2017 |
| WO | WO 2019/153934 A1 | 8/2019 |
| WO | WO 2019/162496 A1 | 8/2019 |
| WO | WO 2019/215199 A1 | 11/2019 |
| WO | WO 2019/238500 A1 | 12/2019 |
| WO | WO 2019/246361 A1 | 12/2019 |
| WO | WO 2020/016616 A1 | 1/2020 |
| WO | WO 2020/089188 A1 | 5/2020 |
| WO | WO 2020/161238 A1 | 8/2020 |
| WO | WO 2020/165456 A1 | 8/2020 |
| WO | WO 2021/55127 A1 | 8/2021 |
| WO | WO 2021/155082 A1 | 8/2021 |
| WO | WO 2021/155103 A1 | 8/2021 |
| WO | WO 2021/155105 A1 | 8/2021 |
| WO | WO 2021/155153 A1 | 8/2021 |
| WO | WO 2021/155170 A1 | 8/2021 |

OTHER PUBLICATIONS

Pogorilyi et al., Russ. J. Appl. Chem. 80(2): 330-334 (2007).*

Sung et al., Proc. Nat'l. Sci. Counc. Repub. China B 13(4): 250-257 (1989).*

Salih et al., J. Engineering 18(9): 1042-1054 (2012).*

PubChem, https://pubchem.ncbi.nlm.nih.gov/compound/3-_3-Chloro-benzenesulfonylamino_-benzoic-acid, accessed Apr. 6, 2024.*

Comstock J., "Healthy.io gets FDA nod for smartphone camera-based home urine test". Jul. 25, 2018; Retrieved from internet on Nov. 18, 2021 at: <https://www.mobihealthnews.com/content/ healthyio-gets-fda-nod-smartphone-camera-based-home-urine-test in 2 pages.

healthy.io; (2020) Turning the smartphone into a medical device, downloaded from the Internet on Jan. 8, 2021, URL: https://healthy.io/services/maternity/ in 3 pages.

Min et al., "Development of a smartphone-based lateral-flow imaging system using machine-learning classifiers for detection of *Salmonella* spp". J Microbiol Meth. Sep. 1, 2021;188: 106288 in 8 pages.

Scanwell Health, "At-Home UTI Test—Know if you have a UTI in 2 minutes", downloaded Jan. 8, 2021 from https://www.scanwellhealth.com/uti in 9 pages.

International Search Report and Written Opinion dated Jan. 24, 2022 for Application No. PCT/US2021/055963 in 9 pages.

International Search Report and Written Opinion dated Jun. 22, 2021 for Application No. PCT/US2021/025789 in 11 pages.

Becton, Dickinson and Company, "BD Receives Emergency Use Authorization for First At-Home COVID-19 Test to Use Smartphone to Interpret, Deliver Results", BD Press Release; Aug. 25, 2021; available online at https://news.bd.com/2021-08-25-BD-Receives-Emergency-Use-Authorization-for-First-At-Home-COVID-19-Test-to-Use-Smartphone-to-Interpret,-Deliver-Results; 2 pages.

Blake et al., "Diagnosis of Porphyria—Recommended methods for peripheral laboratories". The clinical biochemist—Reviews. May 31, 1992 (May 31, 1992). pp. 1-13. XP055768951, Retrieved from the Internet: URL:https://www.aacb.asn.au/documents/item/150 [retrieved on Jan. 26, 2021] Method; p. S7.

Deacon et al., "Identification of Acute Porphyria: Evaluation of a Commercial Screening Test for Urinary Porphobilinogen". Annals of Clinical Biochemistry., vol. 35, No. 6, Nov. 1, 1998, pp. 726-732.

Gorchein, "Testing for Porphobilinogen in Urine," Clinical Chemistry, vol. 48, Issue 3, Mar. 1, 2002, pp. 564-566.

International Search Report and Written Opinion mailed on Dec. 30, 2011, in International Application No. PCT/US2011/001581, 9 pages.

International Search Report and Written Opinion mailed on May 21, 2012, in International Application No. PCT/US2011/059227, 9 pages.

International Search Report and Written Opinion mailed on Mar. 24, 2021, in International Application No. PCT/US2020/060579, 19 pages.

Mauzerall et al., "The Occurrence and Determination of S-Aminolevulinic Acid and Porphobilinogen in Urine," J. Biol. Chem. 1956, 219:435-446.

Moore et al., "A Quantitative Assay for Urinary Porphobilinogen," Clinical Chemistry, vol. 10, No. 12, 1964, pp. 1105-1111.

Roshal et al., "Rapid Quantitative Method Using Spin Columns to Measure Porphobilinogen in Urine," Clinical Chemistry, vol. 54, No. 2, Feb. 1, 2008 (Feb. 1, 2008), pp. 429-431.

Thermo Fisher: "Porphobilinogen (PBG) Test Kit", Catalogue No. TR52001, Dec. 31, 2011 (Dec. 31, 2011), XP055768704, Retrieved from the Internet: URL:https://static.thermoscientific.com/images/D03132~.pdf [retrieved on Jan. 26, 2021] the whole document.

Vogeser et al., "Evaluation of a commercially available rapid urinary porphobilinogen test," Clinical Chemistry and Laboratory Medicine, vol. 49, No. 9, Jan. 1, 2011, pp. 1491-1494.

Bosch; Press Release "Bosch's new rapid coronavirus test delivers reliable results in 39 minutes", dated Jul. 222, 2021; retrieved from https://www.bosch-presse.de/pressportal/de/en/boschs-new-rapid-coronavirus-test-delivers-reliable-results-in-39-minutes-219392.html.

Electronics-Lab; "ST Real-Time PCR Molecular Technology enables detection of genetic materials", dated Aug. 1, 2019; retrieved from https://www.electronics-lab.com/st-to-make-cartridges-for-covid-19-tests/; 1 page.

Genengnews; "Paper-based Immunoassays Gain Currency", Aug. 1, 2019; downloaded from https://www.genengnews.com/insights/paper-based-immunoassays-gain-currency/; 1 page.

(56) References Cited

OTHER PUBLICATIONS

R&D Systems; "ELLA Automated Immunoassay System—Your Next Generation ELISA", dated Jul. 22, 2021; retrieved from https://www.rndsystems.com/products/ella-automated-immunoassay-system_600-100#product-reviews; 1 page.

* cited by examiner

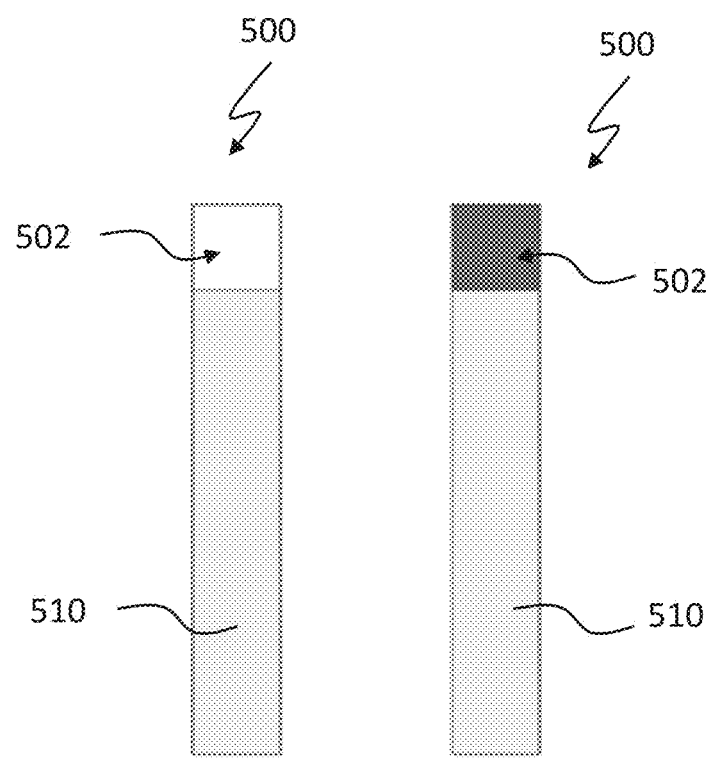

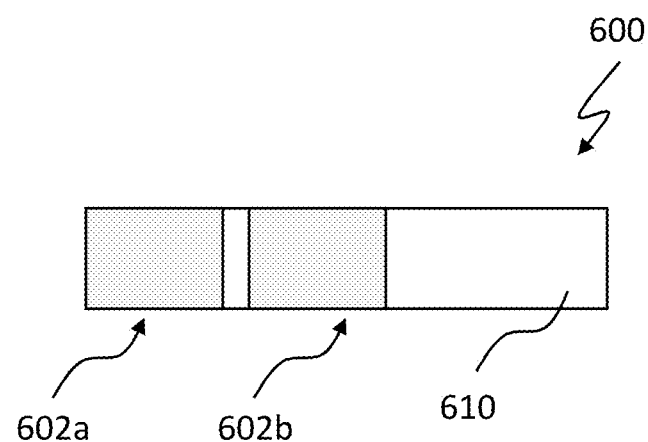
FIG. 6A
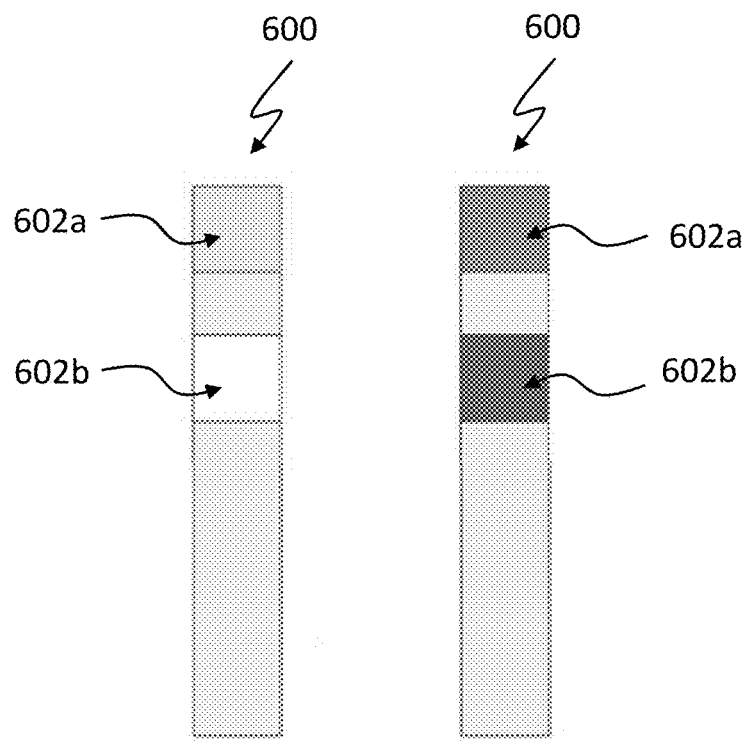
FIG. 6B  FIG. 6C

| Color Label | L | a | b |
|---|---|---|---|
| S1 | 85.94 | -0.37 | 3.05 |
| S2 | 80.41 | 5.4 | -0.67 |
| S3 | 76.16 | 11.08 | -3.6 |
| S4 | 68.11 | 19.75 | -10.07 |
| S5 | 60.48 | 27.53 | -13.85 |

| Color Label | L | a | b |
|---|---|---|---|
| A1 | 87 | 0.1 | 1.16 |
| C3 | 79 | 4.79 | -0.1 |
| G3 | 78 | 6.68 | 1.91 |
| B4 | 74 | 11.78 | -0.45 |
| E2 | 64 | 20 | -7.72 |
| B2 | 58.8 | 29 | -8.28 |
| H1 | 53.8 | 33.34 | -9.35 |
| A3 | 52.1 | 35.7 | -9.83 |
| E1 | 53.2 | 37.8 | -7.13 |

| Reference color blocks | a | Representative PBG concentration (mg/L) |
|---|---|---|
| A1 | 0.1 | 0 |
| C3 | 4.79 | 3 |
| B4 | 11.78 | 6 |
| E2 | 20 | 12 |
| B2 | 29 | 24 |

Correlation of "a" values to PBG concentrations $y = 0.0205x^2 + 0.1969x + 0.6344$
$R^2 = 0.9941$

| Test pad | a | Calculated PBG concentration (mg/L) |
|---|---|---|
| S1 | -0.37 | 0.56 |
| S2 | 5.4 | 2.30 |
| S3 | 11.08 | 5.35 |
| S4 | 19.75 | 12.56 |
| S5 | 27.53 | 21.67 |

FIG. 11C

| Color blocks | Color distance | PBG concentration (mg/L) |
|---|---|---|
| A1-A1 | 0 | 0 |
| A1-G3 | 11.1488295 | 3 |
| A1-B4 | 17.4763383 | 6 |
| A1-E2 | 30.4139771 | 12 |
| A1-B2 | 40.3788311 | 24 |

| PBG test | Distance to A1 | Estimated PBG concentration (mg/L) |
|---|---|---|
| S1 | 1.16 | 0.50 |
| S2 | 8.46 | 1.72 |
| S3 | 15.43 | 4.17 |
| S4 | 27.26 | 11.23 |
| S5 | 38.15 | 20.94 |

(A) 0 mg/L PBG solution
(B) 3 mg/L PBG solution
(C) 6 mg/L PBG solution
(D) 12 mg/L PBG solution
(E) 24 mg/L PBG solution A) Unprocessed urine
B) Urine with the presence of 6mg/L PBG
C) Urine with the presence of 24mg/L PBG
D) Processed urine with the presence of 6mg/L PBG
E) Processed urine with the presence of 24mg/L PBG A) Unprocessed urine
B) Processed urine
C) Unprocessed urine with the presence of 24mg/L PBG
D) Processed urine with the presence of 24mg/L PBG
E) Unprocessed urine with the presence of 12mg/L URO
F) Processed urine with the presence of 12mg/L URO
G) Unprocessed urine with the presence of 4mg/L BIL
H) Processed urine with the presence of 4mg/L BIL

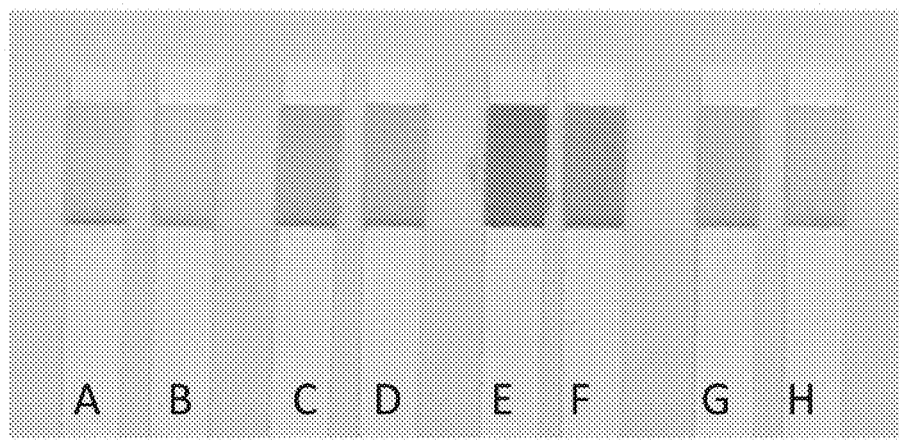

FIG. 15

(A) 100uM PBG
(B) 100uM PBG incubated with 0.2g resins
(C) 100uM PBG incubated with 0.5g resins
(D) 100uM PBG incubated with 1g resins
(E) 100uM URO
(F) 100uM URO incubated with 0.2g resins
(G) 100uM URO incubated with 0.5g resins
(H) 100uM URO incubated with 1g resins

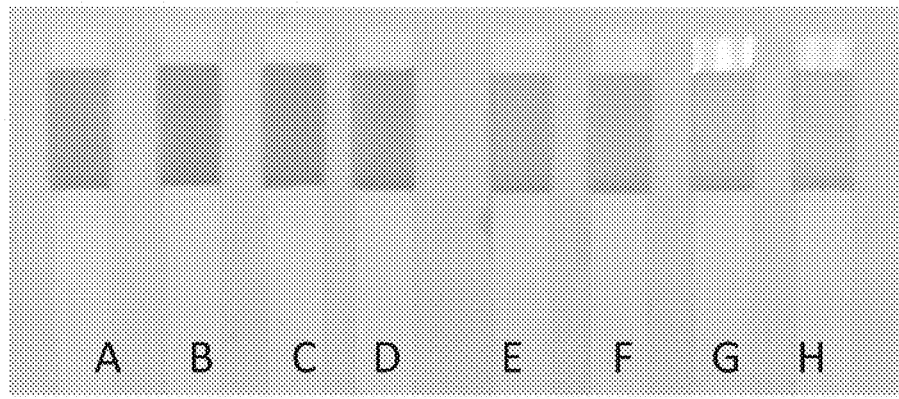

FIG. 16

(A) Unprocessed urine with the presence of 100uM PBG
(B) Processed urine with the presence of 100uM PBG + pass through the resin column
(C) Unprocessed urine with the presence of 100uM Bilirubin
(D) Processed urine with the presence of 100uM Bilirubin + pass through the resin column
(E) Unprocessed urine with the presence of 100uM Biliverdin
(F) Processed urine with the presence of 100uM Biliverdin + pass through the resin column
(G) Unprocessed urine with the presence of 100uM ALA
(H) Processed urine with the presence of 100uM ALA + pass through the resin column
(I) Unprocessed urine with the presence of 100uM Indican
(J) Processed urine with the presence of 100uM Indican + pass through the resin column

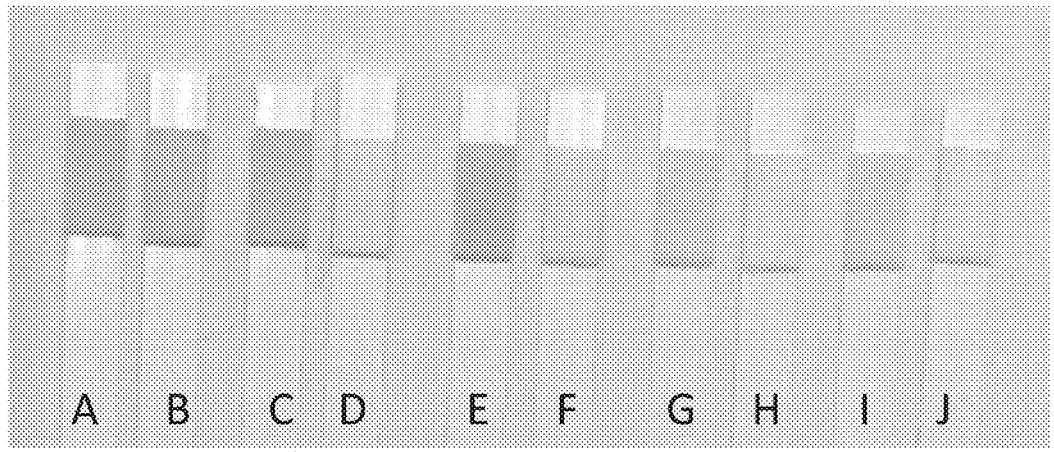

FIG. 17

DIAGNOSTIC TEST KITS FOR SAMPLE PREPARATION AND ANALYSIS

CROSS-REFERENCE TO RELATED APPLICATIONS

This application claims priority to U.S. Patent Application Ser. No. 62/934,655 filed Nov. 13, 2019, which is incorporated herein in its entirety by this reference.

TECHNICAL FIELD

This invention relates generally to the field of sample preparation for diagnostic testing.

BACKGROUND

Substances in bodily fluids such as urine and blood are commonly detected and/or measured for use in diagnostic tests. For example, porphyria is a group of metabolic diseases in which porphyrins accumulate in the body, which negatively affect the skin or nervous systems. Porphyria can lead to detrimental symptoms such as abdominal pain, chest pain, vomiting, high blood pressure, and high heart rate, which may further lead to complications including paralysis and seizures. Porphyria may be diagnosed based on the detection of a high concentration of certain metabolites such as porphobilinogen (PBG) in urine. However, accurate diagnosis of medical conditions relies upon accurate detection of PBG in a patient sample, which may be hampered by interferent substances in the sample. Current test protocols for measuring urinary PBG include removal of interferent substances from a urine sample prior to measuring PBG with the use of a PBG reactive reagent, but these tests are complicated and/or dangerous to perform due to the hazardous chemicals involved, and thus require trained professionals to execute the tests. Furthermore, the volatile nature of chemicals required for preparing samples for existing PBG tests means that such PBG tests must typically be performed in carefully controlled lab conditions or other limited testing environments, which further restricts access to testing and its diagnostic benefits for patients.

Furthermore, even after a sample is prepared and tested with use of a reagent, the test is required to be analyzed using expensive and sophisticated chemistry analyzer lab equipment.

Accordingly, there is a need for new and improved diagnostic test kits for sample preparation and analysis that, for example, provide for easier, safer, more accessible, and/or more accurate diagnostic testing of samples.

SUMMARY

Generally, in some variations, a method for analyzing a sample may include introducing the fluid sample into a vessel comprising a cation-exchange resin, wherein the cation-exchange resin has a high affinity to one or more interferent species in the sample, directing the fluid sample through the cation-exchange resin, thereby capturing one or more interferent species in the cation-exchange resin to purify the fluid sample, and releasing the purified fluid sample from the vessel.

In some variations, the fluid sample may be directed through the cation-exchange resin through a pressure differential generated across the vessel. For example, the fluid sample may be directed through the cation-exchange resin by generating a vacuum within the vessel (e.g., drawing the fluid sample with a syringe coupled to the vessel). In some variations, the method may include incubating the fluid sample in the cation-exchange resin for an incubation period (e.g., 10-15 minutes).

The fluid sample may, in some variations, also be released from the cation-exchange resin (e.g., after the incubation period) through a pressure differential. For example, the fluid sample may be directed through cation-exchange resin by generating a positive pressure within the vessel (e.g., ejecting the fluid sample with a syringe coupled to the vessel).

In some variations, a method for analyzing a sample may additionally or alternatively include one or more other suitable processes for purifying the sample and removing interferents. For example, one or more interferents may be removed with the aid of at least one pre-processing reagent. After the fluid sample is purified, at least a portion of the fluid sample may be applied to a test strip comprising a reagent reactive with an analyte of interest.

By way of example, in some variations a method for analyzing a sample may be performed in relation to a urinary porphobilinogen (PBG) test. In this example, a urine sample may include one or more interferent species such as urea and urobilinogen. The urea may be removed via one or more pre-processing reagents that includes an enzyme (e.g., urease) that consumes urea. Additionally or alternatively, urobilinogen may be removed via an ion-exchange resin device comprising a suitable cation-exchange resin. The cation-exchange resin may, for example, include one or more resins selected from the group consisting of: 1,4-bis(ethenyl)benzene; (4-ethenylphenyl)-trimethylazanium; styrene; chloride, 3-[(3-chlorophenyl) sulfonylamino]benzoic acid, and 1,2-bis(ethenyl)benzene; 1-ethenyl-2-ethylbenzene; styrene. After the sample is purified, at least a portion of the fluid sample may be applied to a test strip comprising a reagent reactive with porphobilinogen.

Generally, in some variations, a system for preparing a fluid sample for testing or other analysis may include a vessel and a cation-exchange resin arranged in the vessel, where the cation-exchange resin is configured to bind to one or more interferent species from the fluid sample to purify the fluid sample. For example, in variations in which the fluid sample is a urine sample intended for a PBG test, the cation-exchange resin may have a high affinity for non-PBG metabolites (e.g., urobilinogen, bilirubin, biliverdin, ALA, and/or Indican) in urine. Examples of suitable cation-exchange resins include one or more resins selected from the group consisting of: 1,4-bis(ethenyl)benzene; (4-ethenylphenyl)-trimethylazanium; styrene; chloride, 3-[(3-chlorophenyl) sulfonylamino]benzoic acid, and 1,2-bis(ethenyl) benzene; 1-ethenyl-2-ethylbenzene; styrene. The vessel may include one or more seals retaining the cation-exchange resin in the vessel (e.g., filters that permit fluid entry into the vessel, but retain the resin). The vessel may include at least one opening configured to couple to a fluid actuation device such as syringe, for directing a fluid sample in and out of the vessel.

Generally, in some variations, a diagnostic test strip for testing a urine sample for porphobilinogen may include a substrate impregnated with a dried solution comprising an acid, a reagent reactive with porphobilinogen (PBG), and one or more stabilizers. The substrate may, for example, include a fiber paper (e.g., cellulose fiber paper) that is laminated onto a backing made of a flexible polymer or other suitable material.

In some variations, the acid may include one or more selected from the group consisting of oxalic acid, maleic acid, and a salicylic-derivative acid.

In some variations, the reagent reactive with PBG may include a benzaldehyde derivative. For example, the reagent reactive with PBG may include one or more selected from the group consisting of: para-Dimethylaminobenzaldehyde, para-Diethylaminobenzaldehyde, 4-(N,N-bis-(2-cyanoethyl)-amino)-benzaldehyde, 4-(N,N-bis-(2-cyanoethyl)-amino)-benzaldehyde, 4-(4-Methylpiperazinyl)benzaldehyde 4-[(2-Cyanoethyl)methylamino]benzaldehyde N-Methyl-N-(2-hydroxyethyl)-4-aminobenzaldehyde, 4-[Bis[2-(acetyloxy)ethyl]amino]benzaldehyde, and 4-(Boc-amino)benzaldehyde.

In some variations, the reagent reactive with PBG may include an Azo dye. For example, the reagent reactive with PBG may include one or more selected from the group consisting of: Fast Red PDC, Fast Red B, Fast Red RC, Fast Red TR, and Fast Blue BB.

Suitable stabilizers in the dried solution may include one or more selected from the group consisting of EDTA, caffeine, borate salt, sodium benzoate, and sodium acetate. Additionally or alternatively, the dried solution may include one or more additives (e.g., to increase bonding of the reagent to the substrate), such as one or more selected from the group consisting of polyvinyl alcohol, polyvinyl pyrrolidone, copolymers of polyvinyl pyrrolidone and polyvinyl acetate, polyglycols, methyl vinyl ether, and maleic anhydride.

Generally, in some variations, a method for analyzing a sample for an analyte of interest (e.g., testing for an analyte of interest) may be performed by one or more suitable processors, such as on a mobile computing device. The mobile computing device may be executing a mobile application for performing the analysis. The method may include receiving an image depicting a diagnostic test region and a color reference chart, where the diagnostic test region indicates a colorimetric reaction with the analyte of interest in the sample. The image may be received, for example, through a mobile application executed on a mobile computing device. In some variations, the method may include calibrating at least a portion of the image based on the color reference chart depicted in the image (e.g., color-correcting based on the color reference chart). The method may further include converting a test region image portion of the image to an analytical color space, determining a first coordinate value and a second coordinate value characterizing the test region image portion in the analytical color space, and quantifying the analyte of interest in the sample based on at least one of the first and second coordinate values, and a predictive formula based on the color reference chart.

The coordinate values characterizing the test region image portion may correspond to a first channel in the analytical color space, and the second coordinate value characterizing the test region image portion may correspond to a second channel in the analytical color space. The analytical color space may include, for example, CIELab or RBG.

In some variations, the color reference chart may include a plurality of reference color blocks associated with known concentrations of the analyte of interest. Furthermore, the predictive formula may be based on reference coordinate values characterizing each of the reference color blocks in the analytical color space. For example, in some variations, the predictive formula may relate at least one reference coordinate value of each reference color block to the known concentration of the analyte of interest associated with each reference color block. This reference coordinate value may be associated with a color channel of the analytical color space (e.g., "a" channel of CIELab). As another example, in some variations, the predictive formula may additionally or alternatively relate a distance in the analytical color space to the known concentration of the analyte of interest associated with each reference color block.

Following determining a quantitative measurement of the analyte of interest, the method may include providing a diagnostic test result based on the quantitative measurement of the analyte of interest.

In some variations, the method for analyzing a sample is performed to quantify porphobilinogen. In these variations, the color reference chart may include a plurality of reference color blocks associated with known concentrations of porphobilinogen, and the predictive formula may be based on reference coordinate values characterizing each of the reference color blocks in a CIELab color space. In some variations, the predictive formula may relate an "a" reference coordinate value of each reference color block to the known concentration of porphobilinogen associated with each reference color block. In some variations, the predictive formula may relate a ratio of "L" and "a" reference coordinate values of each reference color block to the known concentration of porphobilinogen associated with each reference color block. Additionally or alternatively, the predictive formula may relate a distance in the CIELab color space to the known concentration of porphobilinogen associated with each reference color block. The distance may, for example, be distance in a (L, a) plane between a reference color block and a baseline location in the (L, a) plane, such as reference coordinate values of a predetermined reference color block in the color reference chart.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5D and 5E depict schematic views of an example variation of a PBG test strip that is unreacted with PBG and reacted with PBG, respectively.

FIG. 6A depicts a schematic view of an example variation of a test strip with two test regions (e.g., reagent pads).

FIGS. 6B and 6C depict schematic views of an example variation of a PBG and creatinine test strip that is unreacted with PBG and creatinine and reacted with PBG and creatinine, respectively.

FIG. 11C summarizes estimated PBG concentrations for the PBG test strips shown in FIG. 10A, based on the fitted predictive curve shown in FIG. 11B.

FIGS. 13-17 depict examples of sets of PBG test strips exhibiting various colorimetric reactions in response to different urine samples having various combinations of PBG concentration and/or interferent substances, with different kinds of pre-processing performed on the urine sample to remove one or more interferent substances.

DETAILED DESCRIPTION

Non-limiting examples of various aspects and variations of the invention are described herein and illustrated in the accompanying drawings.

Described herein are diagnostic test kits for sample preparation and analysis, as well as methods for performing and analyzing diagnostic tests using test kits.

Diagnostic Test Kits

Figure 1:
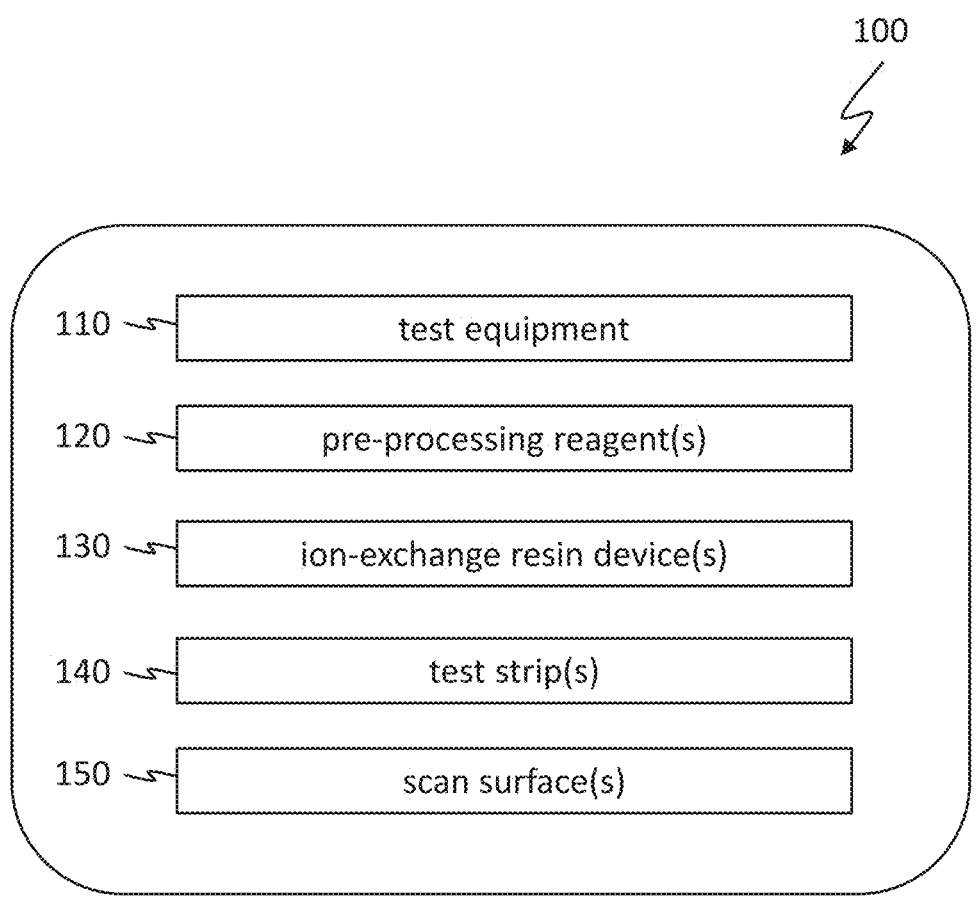
FIG. 1 depicts a schematic of an example variation of a diagnostic test kit.

In some variations, a diagnostic test kit may include one or more components for purifying a sample (e.g., urine, blood, plasma, etc.) and/or one or more components for measuring at least one analyte in the purified sample. Furthermore, the diagnostic kit may, in some variations, include one or more components for supporting computer vision-aided analysis of test results. For example, as shown in FIG. 1, in some variations a diagnostic test kit 100 may include one or more pre-processing reagent(s) 120 and/or at least one ion-exchange resin device 130 to remove one or more interferent substances from a sample. Additionally or alternatively, a diagnostic test kit 100 may include one or more test strips 140 that may include a reagent that is reactive to an analyte of interest in the sample. One or more aids such as a scan surface 150 with a reference color chart (as described in further detail below) may be included in the diagnostic test kit to assist in computer vision-aided interpretation of results depicted on the test strips 140. Furthermore, in some variations the diagnostic test kit 100 may include test equipment 110 such as for manipulating or holding substances such as patient samples and/or reagent(s). For example, the test equipment 110 may include one or more vessels (e.g., vials, cups, trays, etc.), syringes, needles, and/or other accessories for aiding preparation and/or analysis of samples.

The diagnostic test kits are primarily described herein with respect to detecting PBG in a urinary sample. However, it should be understood that other variations may additionally or alternatively include chemicals suitable for preparing and/or analyzing a sample for detection of other suitable analytes. For example, in some variations the diagnostic test kit may be adapted for the detection of urinary aminolevulinic acid (ALA), or the detection of the combination of urinary PBG and ALA.

Figure 2A:
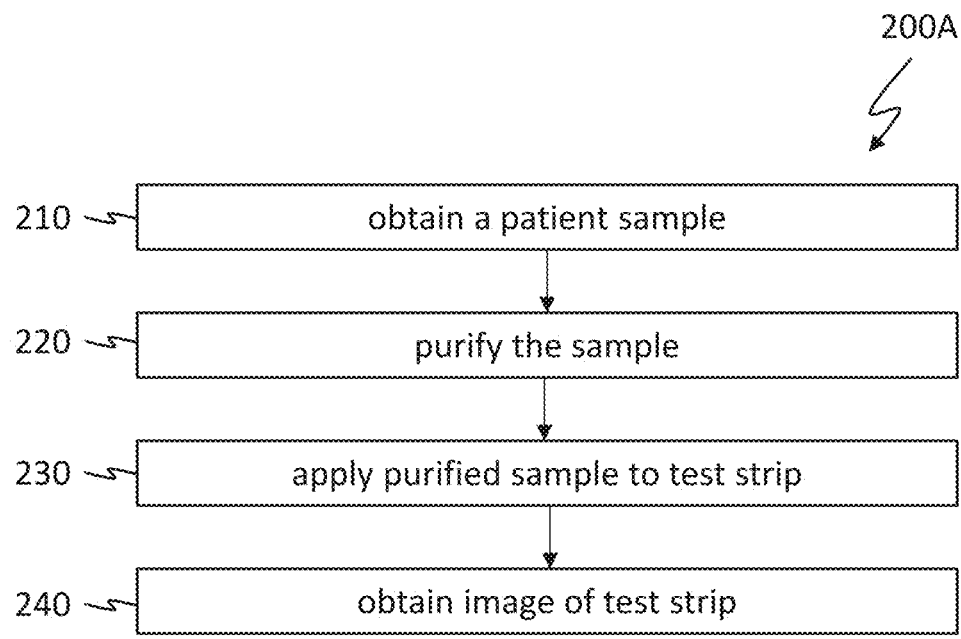
FIG. 2A depicts a flowchart of an example variation of a method of using a diagnostic test kit.

FIG. 2A depicts a flowchart illustrating an example variation of a method of using a diagnostic test kit. Generally, a method 200A of using a diagnostic test kit may include obtaining a patient sample 210 such as urine and purifying the sample 220 by removing one or more interferent substances from the sample. After purifying the sample 220, the method may include applying the purified sample to a test strip 230 including one or more reagents reactive to at least one analyte of interest in the sample. The analyte(s) and respective reagent(s) may react to result in a color change on the test strip, which may be analyzed to evaluate the amount (e.g., concentration) of analyte in the patient sample. In some variations, the method may further include obtaining an image of the test strip 240. The image may further include a depiction of a scan surface with a color reference chart with reference color blocks to aid in computer vision techniques for interpreting colorimetric results of the test strip 240.

Figure 2B:
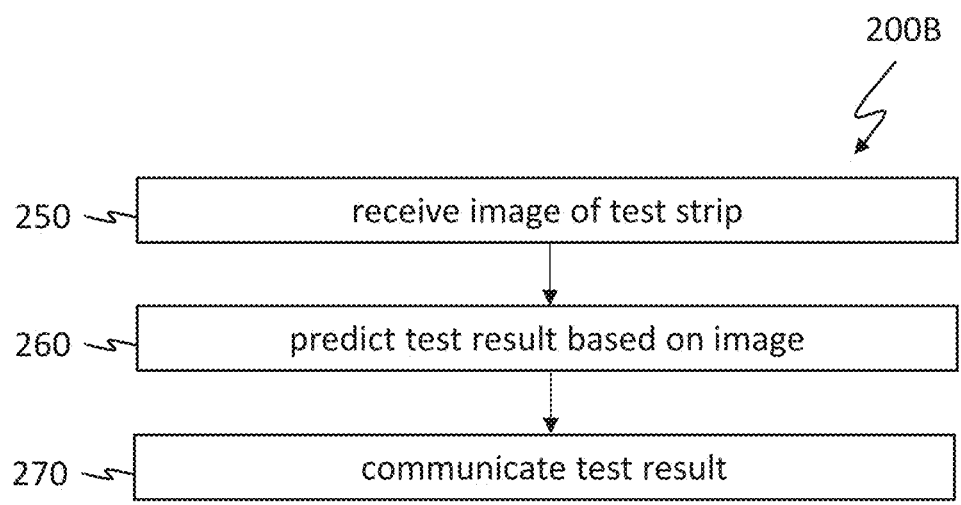
FIG. 2B depicts a flowchart of an example variation of a method of analyzing test results from a diagnostic test kit.

In some variations, the image may be analyzed using one or more computer vision techniques executed by one or more suitable processors. For example, an image of the test strip may be obtained using a suitable computing device (e.g., mobile computing device such as a smartphone, tablet, etc.). The mobile computing device may communicate the image of the test strip via a network (e.g., cellular network, Internet, etc.) to a predictive analysis system that may include one or more processors configured to utilize computer vision techniques to interpret test results from the image of the test strip. Additionally or alternatively, at least a portion of the predictive analysis system may be hosted locally on the mobile computing device. As shown in FIG. 2B, after the one or more processors receives the image of the test strip (250), the processor(s) may predict the test results based on the image (260) using one or more suitable computer vision techniques such as that described below. The predicted test result may be communicated (270) to the patient or another suitable user, such as through a graphical user interface (e.g., part of a mobile application executed on the mobile computing device), notification, e-mail, phone call, and/or in any suitable manner.

Various components of the diagnostic test kit and their use are described below, particularly with reference to an example variation of a diagnostic test kit for testing urinary PBG. The use of such components is further described with reference to the example variation of a method 300 for using a diagnostic test kit shown in FIG. 3.

Pre-Processing Reagents

As described above, in some variations the diagnostic test kit may include one or more pre-processing reagents 120. For a urinary test (e.g., urinary PBG test, aminolevulinic acid test, etc.), it may be desirable to remove urea, a main component of urine that may be an interferent substance. For example, urea may react to the reagent(s) reactive to the analyte of interest, which obscures the true measurement of the analyte of interest in a urine sample. Accordingly, it may be important in some variations to remove urea from the urine sample before testing the sample for the analyte of interest.

In some variations, the pre-processing reagent(s) may include urease, an enzyme that reacts specifically with urea and converts it into ammonia and water. In contrast to existing urinary tests that remove urea with urease in a solution form or using an ion-exchanging column, in some variations the diagnostic test kit 100 may include urease in a dry powder form. This dry powder form may be advantageous for various reasons. For example, while the reactivity of urease in a solution form tends to decrease over time (especially if kept at room temperature), dry powder urease is able to better maintain its reactivity before use. Furthermore, because dry powder urease can better maintain its reactivity over time, dry powder urease has improved shelf life and is more robust against degradation during test kit packaging, storage, and shipping. As described in further detail below, dry powder urease is easy to use, as it can be simply reconstituted into liquid with the addition of water (e.g., water present in a urine sample, or separate volume of water).

In some variations, the pre-processing reagent may be a mixture including one or more additives added to the dry powder urease to improve reagent performance for removing urea. For example, one or more buffer salts such as Tris and/or phosphate may be added to the dry powder to maintain the pH once the dry powder is reconstituted into liquid. Additionally or alternatively, one or more stabilizers may be added to the powder to extend the storage condition of the reagent. For example, suitable stabilizers include Trehalose, BSA, and Cyclodextrin.

In some variations, the diagnostic test kit may include at least an amount of urease that is between about 30 U/mg and about 300 U/mg, which may be sufficient to completely consume total urea in about a 2 ml sample of urine. Other components such as buffer salts and stabilizers may be combined with the dry powder urease in appropriate ratios. In an exemplary variation, the pre-processing reagent may include dry powder urease, trehalose, BSA, and Cyclodextrin in a weight ratio of 1 to 1-10 to 0.1-0.5 to 1-5, which can maintain the urease reactivity for at least 12 weeks at 37° C. In some variations, the pre-processing reagent may be pre-measured and pre-packaged as a mixture (e.g., pre-packaged in a test vial or other suitable container, or in an envelope or other suitable package that may be easily emptied into a suitable container).

Ion-Exchange Resin Device

The diagnostic test kit may further include at least one ion-exchange resin device 130 to further remove other interferent substances in a patient sample. For example, to prepare a sample for a PBG test, it may be beneficial to remove metabolites in urine that are formed during heme biosynthesis alongside PBG but share similar chemical structure to PBG and also react with PBG-reactive reagents. If left in the urine sample, these similar metabolites would interfere with the reactions that would indicate concentration of PBG in the sample. Ion-exchange resins with more affinity to the interferent metabolites than to PBG can help purify the sample.

However, conventional ion-exchange techniques for PBG tests have many drawbacks. Conventional ion-exchange methods for PBG tests utilize an anion-exchange resin, where PBG at a pH of 8-10 exhibits a higher affinity to the anion-exchange resin, compared to other interferents. Accordingly, during the purification process, the urine sample must be adjusted to a higher pH with ammonia, then added to a column that includes anion-exchange resins. The anion-exchange resins selectively filter the urine, as PBG present in the urine binds to the anion-exchange resins while interferents pass through the resins. Thereafter, the resins must be washed thoroughly with buffer, typically with at least three to four rounds of washing in which buffer is slowly drained by gravity, to more fully remove the interferents and also neutralize pH. The resin-bound PBG is then eluted with a weak acid such as acetic acid, to flush the desired PBG for use in the PBG test. The above sequence of steps is not only very time-consuming, but it is also complicated to perform. Care must be taken when handling the necessary hazardous chemicals such as ammonia and acetic acid, which limits who can perform sample purification using these conventional methods. Additionally, due to the repeated wash cycles involved, some PBG can be washed away, which reduces the recovery rate of PBG and compromises the sensitivity of the PBG test. Furthermore, because conventional ion-exchange resin devices for PBG tests require storage in a cool, refrigerated environment and include resins packed with buffer that must be drained prior to use of the ion-exchange resin device, conventional ion-exchange resin devices are typically challenging to make, store, and use.

In contrast to conventional ion-exchange techniques, the diagnostic test kit 100 may include an ion-exchange resin device 130 that is easier and safer to make, store, and use, and also avoids compromise of the sample. In some variations, the ion-exchange resin device may include a vessel and a cation-exchange resin arranged in the vessel and configured to bind through adsorption to one or more interferents from a fluid sample to purify the fluid sample. The cation-exchange resin may be packed in the vessel such that a fluid sample entering the vessel also must pass into the cation-exchange resin. During passage of the fluid sample into or through the cation-exchange resin and/or an incubation period in which the fluid sample is in the cation-exchange resin, the cation-exchange resin may extract interferent substances from the fluid sample without binding to an analyte of interest in the sample. Accordingly, the cation-exchange resin advantageously enables the ion-exchange resin device 130 to purify samples without requiring pH treatment of the sample, buffer wash cycles, elution of captured PBG, etc. that are required by conventional ion-exchange techniques. As a result, the ion-exchange resin device 130 is also easier and safer to use. Furthermore, the ion-exchange resin device 130 may be in a dry format and stored long-term at room temperature (e.g., sealed in a pouch to help protect against contamination).

The specific type of cation-exchange resin in the ion-exchange resin device may depend on the nature of interferent substances to be bound and removed from the fluid sample, and/or on the nature of the analyte of interest to be retained in the moving fluid sample. For example, in an ion-exchange resin device for use in preparing a urine sample for a urinary PBG test, the cation-exchange resin may include one or more of: 1,4-bis(ethenyl)benzene; (4-ethenylphenyl)-trimethylazanium; styrene; chloride, 3-[(3-chlorophenyl)sulfonylamino]benzoic acid, and 1,2-bis(ethenyl)benzene; 1-ethenyl-2-ethylbenzene; styrene. The resin may have any suitable mesh size such as between about 50 and about 800, or about 400. These cation-exchange resins have high affinity for interferent metabolites in relation to a PBG test, such as urobilinogen, such that these cation-exchange resins bind or capture undesired metabolites while allowing PBG to be freely moving in the urine sample. Additionally, in variations in which a urine sample is pre-processed with one or more pre-processing reagents as described above (e.g., to remove urea), the pH of the pre-processed urine may change such that these cation-exchange resins have high affinity to certain other interferent substances. For example, during urine pre-processing as described above, ammonia is generated as a result of enzyme(s) consuming urea, which causes the pre-processed urine to have a higher pH (e.g., between about 8 and about 10). Under such basic pH condition, other interferent substances such as urobilinogen, bilirubin, biliverdin, etc. exhibit higher affinity to cation-exchange resins when compared to PBG. Accordingly, such cation-exchange resins may be capable of retaining a range of undesired metabolites without binding PBG.

Additionally or alternatively, the cation-exchange resin may have a high affinity to one or more analytes of interest, such as ALA. Accordingly, a diagnostic test kit adapted for the detection of ALA (either alone or in combination with another analyte of interest such as urinary PBG, for example) may include an ion-exchange resin device that includes a cation-exchange resin that binds and retains an analyte of interest that may be later eluted with a solution for testing. For example, a urine sample (which may, for example, be pre-processed with one or more pre-processing reagents such as that described above) may be passed through the ion-exchange resin device and retained in the cation-exchange resin. ALA may subsequently be eluted with a suitable weak acidic solution such as sodium acetate for testing. In variations in which both PBG and ALA are analytes of interest, non-PBG metabolites may be removed from the urine sample as described above to generate a urine sample with PBG suitable for a PBG test, then ALA may be eluted from the ion-exchange to generate a fluid volume with ALA that is suitable for an ALA test.

Figure 4A:
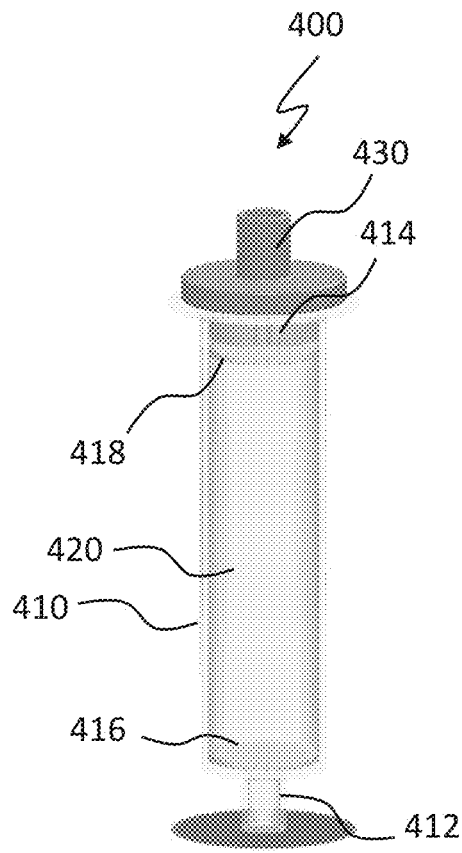
FIGS. 4A and 4B depict perspective and cross-sectional schematic views, respectively, of an example variation of an ion exchange resin device for purifying a sample.
Figure 4B:
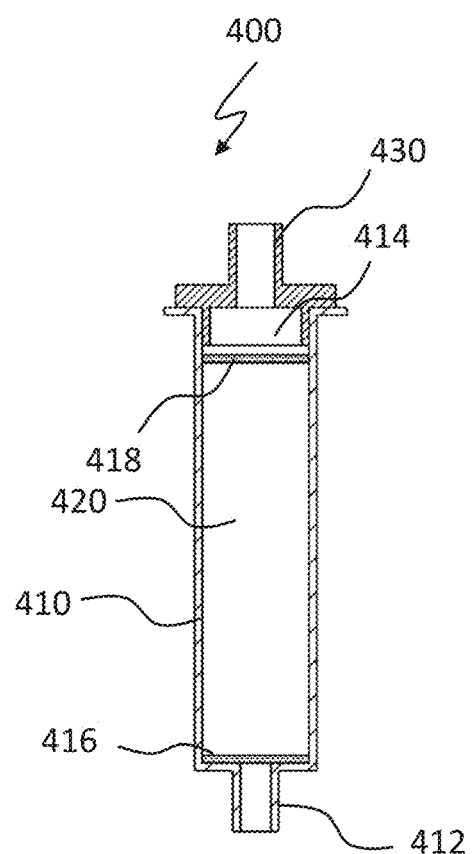

An example variation of an ion-exchange resin device is shown in FIGS. 4A and 4B. As shown in FIGS. 4A and 4B, an ion-exchange resin device 400 may include a vessel 410 and a cation-exchange resin 420. The vessel 410 may include a volume in which the cation-exchange resin may be arranged between a first opening 412 and a second opening 414 of the vessel 410. The first opening 412 and the second opening 414 may be in fluidic communication with the volume containing the cation-exchange resin. In some variations, the cation-exchange resin may be packed without buffer, which further simplifies manufacture of the device. The volume containing the resin 420 may be sealed to help retain the resin 420 within the volume and prevent leak of resin particles from the vessel 410, such as sealed at the first and second ends. For example, in some variations the ion-exchange resin device 400 may include a first seal 416 arranged at or near the first opening 412 of the vessel and a second seal 418 arranged at or near the second end 414 of the vessel. The seals may include any suitable seal, such as a frit, filter or other mesh with pore size smaller than resin particles, etc. In some variations, at least one of the openings of the vessel 410 may include a fitting 430 (e.g., luer lock adaptor) configured to enable coupling of a syringe, pump, or other suitable fluid actuating device to the vessel 410, such that the fluid actuating device may draw or otherwise force a fluid sample through the cation-exchange resin for purification. Alternatively, in some variations the fluid actuating device 440 (e.g., syringe) may be pre-attached or integrally formed with the vessel 410.

The ion-exchange resin device may have any suitable size and shape. In some variations, the ion-exchange device is sized with a volume large enough to accommodate a desired or predetermined fluid sample volume (e.g., at least 2 ml, at least 3 ml, at least 4 ml, at least 5 ml, etc.). For example, in some variations, the volume may be columnar-shaped (e.g., the vessel 410 may include a column) and the first and second openings may be arranged and first and second ends of the column, respectively. The column may have a diameter between about 10 mm and about 20 mm, and a height between about 50 mm and about 70 mm. Between about 0.5 g and about 2 g of suitable cation-exchange resin may be packed and sealed into the vessel, and have a mesh size between about 50 and about 800, or about 400.

In other variations, the ion-exchange resin device may have other suitable form factors including a cation-exchange resin. For example, in some variations the ion-exchange resin device may include a cation-exchange resin placed or preloaded into a cup (e.g., urine collection cup), vial, beaker, or other suitable container. In some variations, the cation-exchange resin may be retained with a permeable bag, membrane (e.g., fabric) or other suitable barrier. The urine sample may, for example, be deposited into such containers and allowed to interact with a cation-exchange resin similar to that described above, then decanted, pipetted, or otherwise removed from the container.

Test Strips

Figure 5A:
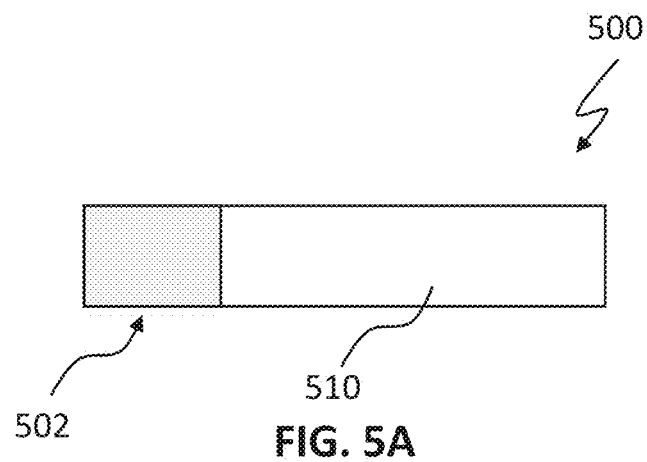
FIGS. 5A-5C depict a top plan view, a side view, and an exploded view, respectively of an example variation of a test strip.
Figure 5B:
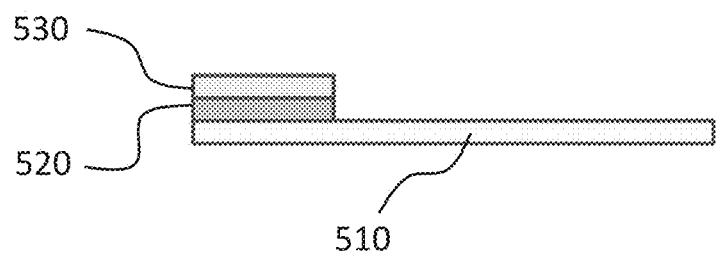

As described above, the diagnostic test kit 100 may further include one or more test strips with at least one reagent that is reactive with the analyte of interest. The test strip may have a dry format, in that the test strip may include a cellulose fiber paper other suitable substrate that is impregnated with a dried solution including a reagent reactive with the analyte of interest. Examples of suitable cellulose fiber paper are Whatman 903 or 593, which may have a thickness between about 0.3 mm and about 1 mm, for example. The dried test strip may be stable and suitable for long-term storage. As shown in FIGS. 5D and 5E, a test strip 500 may include a test region 502 including the reagent-impregnated substrate, such that presence between the reagent and the analyte of interest in a sample may result in a visible color change. For example, FIG. 5A illustrates a schematic of an unreacted test strip 500 with a white test region 502, while FIG. 5B illustrates a schematic of the test strip 500 reflecting exposure to a fluid sample with a significantly high concentration of the analyte of interest. The resulting color post-reaction may be indicative of concentration of the analyte of interest in the sample, and thus may be evaluated as described in further detail below to provide a diagnostic test result relating to the analyte of interest.

In some variations, the test strip is specific for a PBG test by including at least one PBG reactive reagent. For example, the PBG reactive reagent may include one or more benzaldehyde derivatives, such as para-Dimethylaminobenzaldehyde (DMAB, or Ehrlich's reagent), para-Diethylaminobenzaldehyde, 4-(N,N-bis-(2-cyanoethyl)-amino)-benzaldehyde, 4-(N,N-bis-(2-cyanoethyl)-amino)-benzaldehyde, 4-(4-Methylpiperazinyl)benzaldehyde 4-[(2-Cyanoethyl)methylamino]benzaldehyde N-Methyl-N-(2-hydroxyethyl)-4-aminobenzaldehyde, 4-[Bis[2-(acetyloxy)ethyl]amino]benzaldehyde, 4-(Boc-amino)benzaldehyde, other benzaldehyde derivates, and/or any combination thereof. As another example, the PBG reactive reagent may additionally or alternatively include one or more Azo dyes such as Fast Red PDC, Fast Red B, Fast Red RC, Fast Red TR, Fast Blue BB, and/or any combination thereof.

The mechanism of benzaldehydes, which condenses with the aromatic amines from PBG, involves the condensation of the aldehydes to release the oxygen molecule. The oxygen molecule combines with the amine group to form the Schiff's base in the presence of acidic medium, which promotes the electron resonance of the aromatic ring. The formed complex absorbs the light at between about 500 nm and about 550 nm, which results in a magenta color. Thus, to facilitate an acidic reactive environment on the test strip, the PBG test strip may also be impregnated with one or more acids, such as an oxalic acid, maleic acid, salicylic-derivative acid, and/or any combination thereof.

In some variations, the test strip may further be impregnated with one or more additives. For example, the additives may include stabilizers that help maintain the integrity of the reactive reagent, such as benzaldehyde derivatives that tend to be oxidized and lose their reactivity over time. Examples of stabilizing additives include EDTA, caffeine, borate sale, sodium benzoate, sodium acetate, and/or combinations thereof.

As another example, additives may include one or more bonding aids (e.g., bonding polymers) that increase the bonding strength of the reactive reagent to the substrate. Examples of bonding aids include polyvinyl alcohol, polyvinyl pyrrolidone, copolymers of polyvinyl pyrollidone and polyvinyl acetate, polyglycols, methyl vinyl ether, maleic anhydride, and/or combinations thereof.

Furthermore, additives applied to the test strip may include one or more substances to increase the drying efficiency of the solution impregnated on the test strip. Examples of such substances include readily volatile solvents such as methanol, ethanol, acetone, isopropanol, dimethylformamide, tetrahydrofuran, and/or combinations thereof. These volatile solvents may be mixed with the aqueous reagent in solvent-reagent volume ratios ranging between, for example, about 1:1 to about 1:10.

In some variations, the PBG test strip may be made by generating a solution with the PBG reactive reagent, one or more acids, and one or more additives, and then impregnating the reagent solution onto a fiber paper, which is then dried. For example, to make the reagent solution, a suitable mount (e.g., between about 30 g and about 80 g) of solid acid may be dissolved into about 100 ml or other suitable volume of water to acidize the solution. A suitable amount (e.g., between about 1 g and about 5 g of PBG reactive reagent) may be added to the acidic solution, followed by additives. In some variations, the reagent solution to be applied to the fiber paper may include PBG reactive reagent, EDTA, caffeine, borate salt, sodium benzoate, and bonding aids in a ratio of 1 to 0.5-1 to 1-10 to 0.5-1 to 0.5-1 to 1-10, respectively. The reagent solution may then be impregnated on a fiber paper and allowed to dry. As described above, in some variations, the reagent solution may include one or more additives to increase the efficiency of the drying process.

Figure 5C:
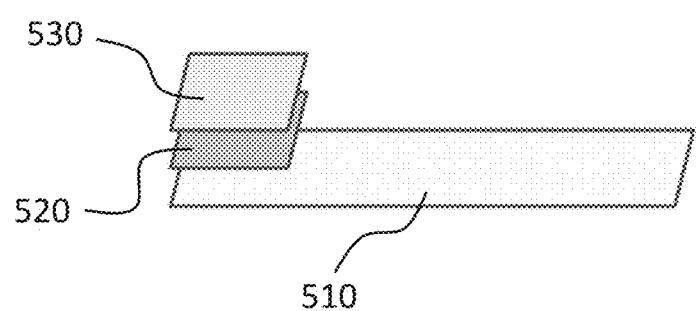

After the impregnated fiber paper substrate is dried, pieces of the fiber paper substrate may be laminated onto strips of plastic backing to form assembled test strips. Plastic backing material can include, for example, PVP or PET with a sufficient thickness (e.g., between about 0.25 mm and about 0.5 mm thick) so as to be rigid enough to support the cellulose fiber paper. In some variations, double sided tape with acrylic or acrylate adhesive materials can be used for the lamination. For example, as shown in FIGS. 5A-5C, a test strip 500 may include a strip of plastic backing 510 and a test region 502 including a fiber paper substrate 520 laminated between the backing 510 and a laminate covering 530. In some variations, a larger sheet of fiber paper may be impregnated with the reagent solution as described above and then cut into smaller pieces prior to lamination onto the backing strips. Alternatively, in some variations the fiber paper may be pre-cut into smaller pieces prior to impregnation with the reagent solution and lamination. Although the test strip shown in FIGS. 5A-5C is rectangular, it should be understood that the test strip may have any suitable shape (e.g., square, circular, etc.). Furthermore, while the test strip 500 includes a single test region 502 on the backing, in some variations, a test surface may include multiple test regions 502. For example, a test sheet may include multiple test regions 502 arranged in an array, where each test region 502 may correspond to a different fluid sample (e.g., different patients, or same patient for redundancy, etc.).

In some variations, the test strip may additionally or alternatively include at least one test region that is configured to detect creatinine in urine. Creatinine is a waste product produced by muscles and may be indicative of kidney disease. In a healthy person, creatinine is excreted into the urine at a constant rate. Therefore, urine creatinine level may be an indicator of level of urine concentration in the sample. Such a test region on a creatinine test strip may include one or more reagents that are reactive to creatinine. For example, in some variations a creatinine test strip may include a reagent solution including lithium hydroxide and/or nitro-benzoic acid derivative. Additional additives such as a buffer and/or other non-reactive ingredients (e.g., any of the additives described above) may further be included in the reagent solution in the test strip. The creatinine test strip may be made in a manner similar to that described above, but with substances reactive to creatinine. For example, in some variations the reagent solution to be applied to the fiber paper may include about 2.5% w/w lithium hydroxide, about 4.5% w/w nitro-benzoic acid derivative, about 56.4% w/w buffer, and about 36.6% w/w non-reactive ingredients.

Furthermore, in some variations, a test strip may include multiple test regions that are configured to test for multiple analytes of interest. For example, as shown in FIG. 6A, a test strip 600 may include a first test region 602a and a second test region 602b arranged on a backing 610 similar to that described above. The first test region 602a may include a reagent reactive to a first analyte of interest, and the second test region 602b may include a reagent reactive to a second analyte of interest. Multiple test regions for estimating concentration of multiple analytes of interest may, for example, provide additional diagnostic insight based on ratios of multiple analytes present in a sample. For example, one of the test regions may include a reagent reactive to PBG (e.g., as described above), and the other of the test regions may include a reagent reactive to creatinine. As shown in FIGS. 6B and 6C, both of the test regions 602a and 602b may undergo a color change that are indicative of amount of creatinine and PBG, respectively. Measurement of a PBG to creatinine ratio may, for example, be helpful to standardize urine PBG levels against 24-hour urine specimens. If the tested urine sample is highly concentrated, a false positive PBG test result might occur. However, as described above, urine creatinine level may inform the level of urine concentration in the tested urine sample, allowing for normalization based on urine concentration. For example, the result of the spot urine PBG test on the test strip may be normalized with per gram of urine creatinine, thereby increasing the accuracy of the PBG test. Accordingly, the 24-hour urine test may not be necessary.

Scan Surface(s)

As described above, the diagnostic test kit 100 may include one or more scan surfaces which may be placed behind or proximate any suitable diagnostic test (e.g., in the same field of view of a camera) as an aid for computer vision-based analysis. The scan surface may, for example, be located on a card, tray, mat, pedestal, housing, instruction booklet, or any suitable physical structure configured to receive a diagnostic test. The scan surface may be formed on paper, plastic, cardboard, or other suitable material. In some variations, the scan surface may be affixed to an organizer device such as that described below. When imaged together in the same field of view as a test strip containing a sample for diagnostic testing, the scan surface may aid computer vision-based techniques to identify the test strip (and test region or reagent pad of the test strip)

Figures 7A, 7B:
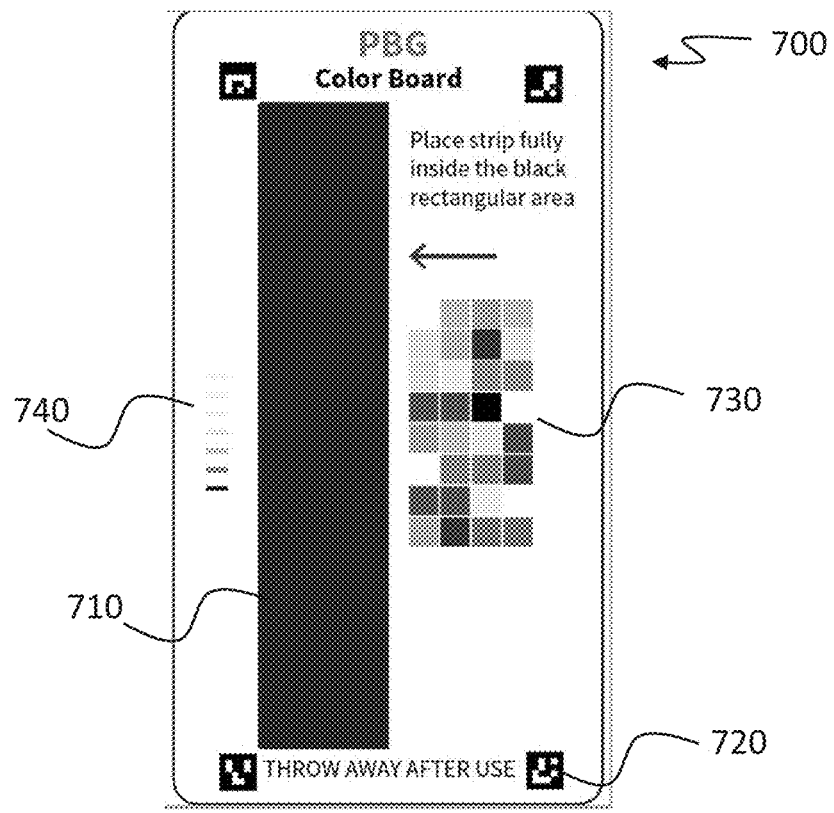
FIG. 7A depicts an example variation of a scan surface in a diagnostic test kit.
FIG. 7B depicts an example variation of a color reference chart with reference color blocks.

As shown in FIG. 7A, an example variation of a scan surface may include a test placement guide 710 indicating placement of a diagnostic test against the scan surface for imaging, and/or a color reference chart 730 including reference color blocks. At least a portion of the scan surface (e.g., the test placement guide 710) may include an absorbent material to help remove excess fluid sample from the test strip. Furthermore, the test placement guide 710 may, in some variations, have a contrasting background (e.g., a dark background against a light-colored diagnostic test) to help aid computer-vision techniques identify the diagnostic test strip in the image and/or the test region on the test strip whose color is to be evaluated.

The color reference chart 730 may include reference color blocks, each of which represents a value or range of analyte concentration (e.g., PBG concentration). In some variations, the nature and use of reference color blocks on the color reference chart may be similar to that described in U.S. Pat. Nos. 8,655,009 and 8,911,679, each of which is incorporated herein by reference. Generally, the color formed on the reagent pad or test region of the diagnostic test strip may be analyzed (e.g., determining color space coordinates of the developed color on the test strip) and matched to at least one reference color block on the scan surface to obtain an estimate of the analyte concentration. As shown in the example of FIG. 7B, in some variations, the color reference chart may include reference color blocks that are mapped to internal codes (e.g., A1 through H4) for easy identification and referencing of each reference color block, such as according to relative location on the color reference chart. The color reference chart 730 may be on the same scan surface (e.g., same scan card) as the test placement guide 710 as shown in FIG. 7A, or may be appear on a separate scan surface.

Various other fiducials may additionally or alternatively be included on the scan surface to aid computer vision techniques, as further described below. For example, in some variations, the scan surface may include one or more spatial markers 720 that function to help facilitate spatial locating and/or identification of the spatial orientation of the diagnostic test strip and/or its test region (e.g., reagent pad) within the image. In some variations, the spatial markers may be located in and/or around the test placement guide (that is, a region of the scan surface expected to receive a diagnostic test) in an arrangement that defines a boundary of the diagnostic test in the image. By identifying the spatial markers, this boundary around the diagnostic test strip and/or color reference chart may be identified, thereby enabling cropping of image to isolate the test region for further analysis without interference from the background of the image. For example, the scan surface may include at least three spatial markers that form vertices of a bounded area. Generally, the spatial markers may include any suitable fiducial, such as ArUco markers, QR code markers, other computer-readable markers, or custom markers with sufficiently contrasting visual characteristics.

Figure 8:
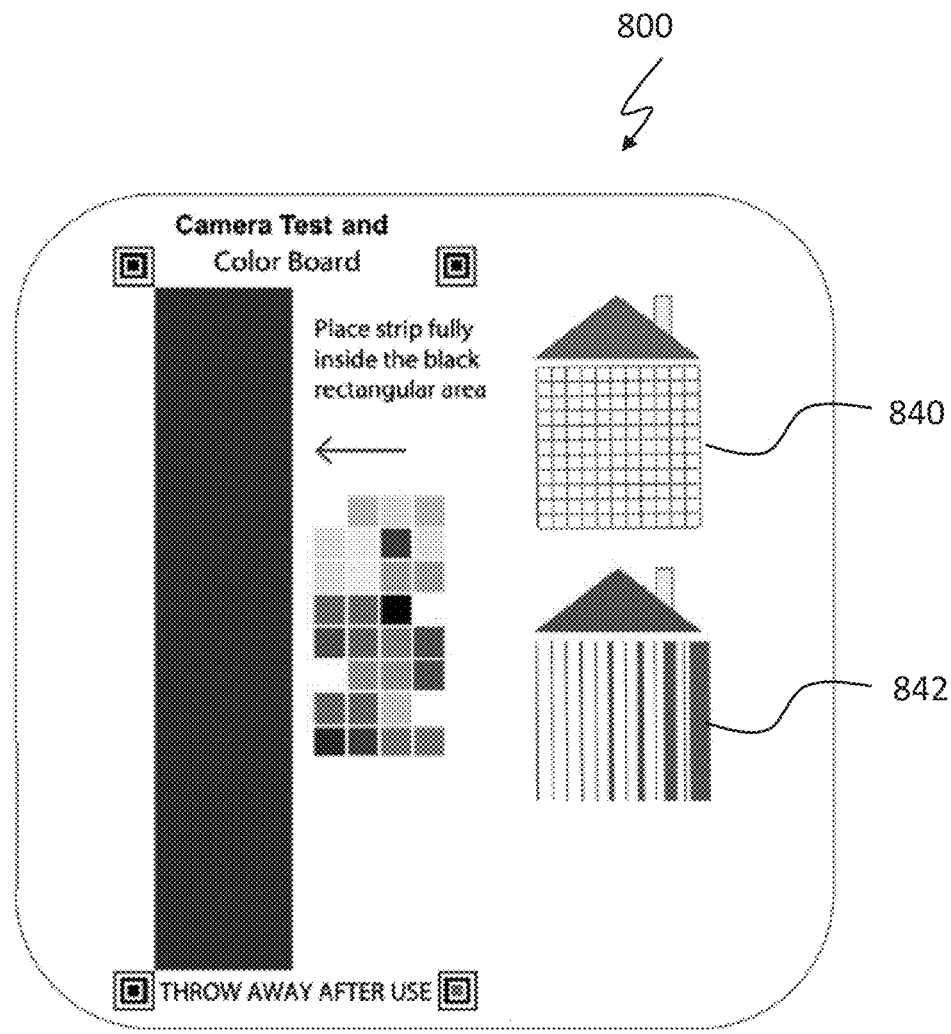
FIG. 8 depicts an example variation of a scan surface with calibration markings.

In some variations, the scan surface may include other suitable markers for calibration or other reference. For example, the scan surface may include standard color and/or grayscale markings 740 that may function as a reference for automatic color correction (e.g., white balance) by an image sensor, so as to reduce the influence of illuminant conditions that may interfere with accurate test result interpretation. White areas on the scan surface may additionally or alternatively be used by white balancing algorithm(s). Other calibration markings may include patterns such as grids, lines set at different distance apart, lines of different thickness, etc., to test camera characteristics such as resolution, distortion, and blur. As shown in FIG. 8, such calibration markings 840 and 842 may appear in a decorative manner embedded in graphical design of the scan surface.

Additionally or alternatively, such calibration markers may appear on any suitable surface, such as a surface that is separate from the scan surface for receiving the diagnostic test. For example, color calibration markers may be present on a separate calibration card that may be referenced separately and prior to imaging the diagnostic test on the scan surface. Other fiducials and markings for a scan surface are described in further detail in U.S. Patent App. No. 63/079,975, which is incorporated herein by this reference.

Any of the visual features on the scan surface (e.g., test placement guide, spatial markers, calibration markers, other fiducials, etc.) may be printed or otherwise applied directly onto the scan surface or on a decal that is applied to the scan surface. For example, the visual features may be printed in ink (e.g., color ink, black ink, etc.), paint, and/or laser jet toner, etc. In some variations, the visual features may be printed in a digital printing process, a plate printing process, and/or other suitable printing process(es).

Organizer Device

In some variations, some or all of the components in the diagnostic test kit 100 may be arranged in an organizer device that helps organize the components and/or guide a user in performing a method using the diagnostic test kit. For example, the organizer device may include receptacles (e.g., cavities, depressions, holes, etc.) that are arranged in a sequential order (e.g., linear, clockwise, counter-clockwise, etc.) corresponding to the order of user of those components. Additionally or alternatively, the receptacles for kit components may be labeled to further indicate the purpose or function of the kit components. In some variations, the organizer device may additionally or alternatively include one of more guides configured to hold components during use of such components, such as a test container holding a pre-processing reagent to which a patient sample may be added, or an ion-exchange resin device such as that described above.

Furthermore, in some variations, the organizer device may include a surface that incorporates a scan surface with a color reference chart as described above, or provides a backing against which the scan surface with a color reference chart may be affixed (e.g., with adhesive). Additionally or alternatively, the organizer device may include a ledge, slot, or the like on which a separate scan surface (e.g., scan card) and/or test strip may rest. Accordingly, the organizer device may include features that may help arrange both the test strip and the scan surface in the same field of view of a camera.

Figure 9:
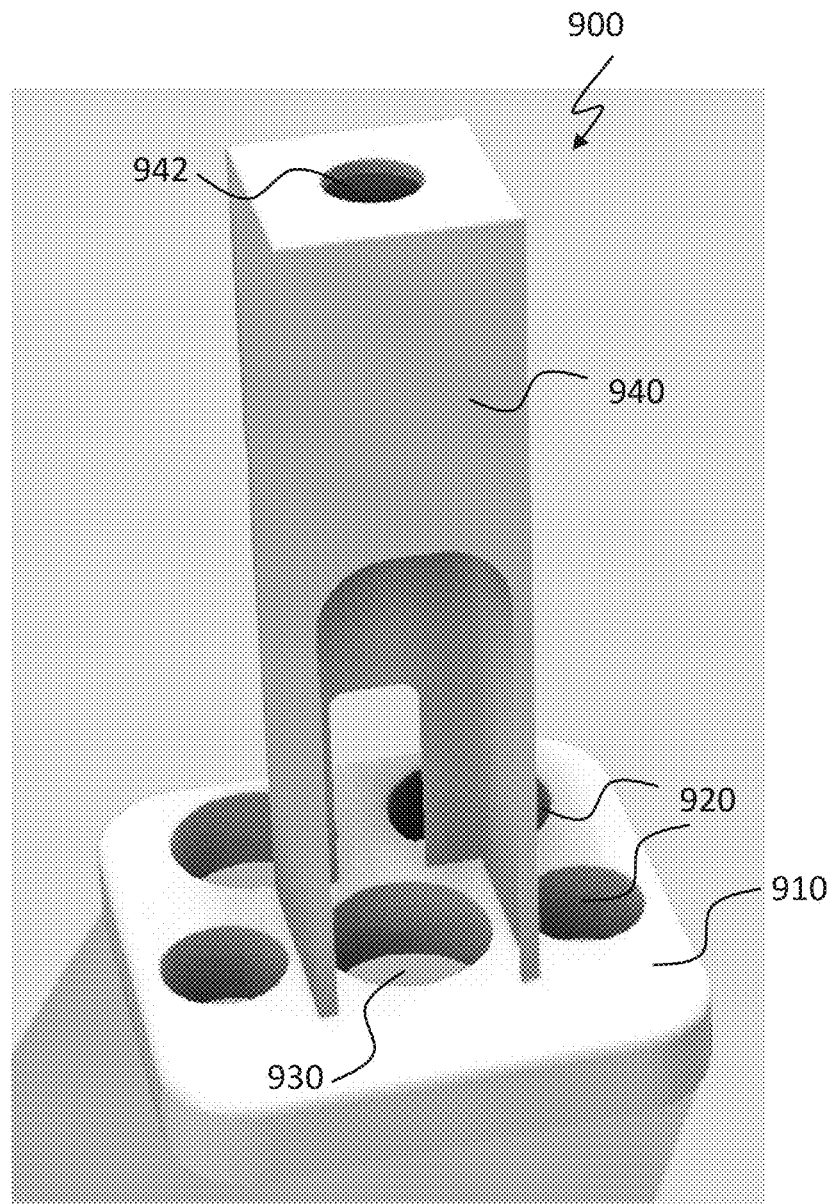
FIG. 9 depicts an example variation of an organizer configured to guide placement and use of diagnostic test kit components.

An example variation of an organizer device 900 is depicted in FIG. 9. As shown in FIG. 9, the organizer device 900 may include a base 910 and a tower 940. The base 910 may have a flat or level underside configured to rest on a flat surface such as a tabletop. The base 910 may include one or more cavities 920 configured to hold components (e.g., reagents) in the order in which they are used. The tower 940 may include an internal channel configured to receive an ion-exchange resin device such as that described above, as well as a syringe or similar device operable with the ion-exchange resin device that which may extend through a syringe plunger hole 942 for actuation by a user. One or more similar cavities or other receptacles may be arranged in the base or other feature of the device 900 to hold items such as a sample container, test strip(s), etc. For example, central cavity 930 may be configured to receive a container for a urine sample to be drawn into an ion-exchange resin device, as described in further detail below.

Example Method of Performing a Diagnostic Test

Figure 3:
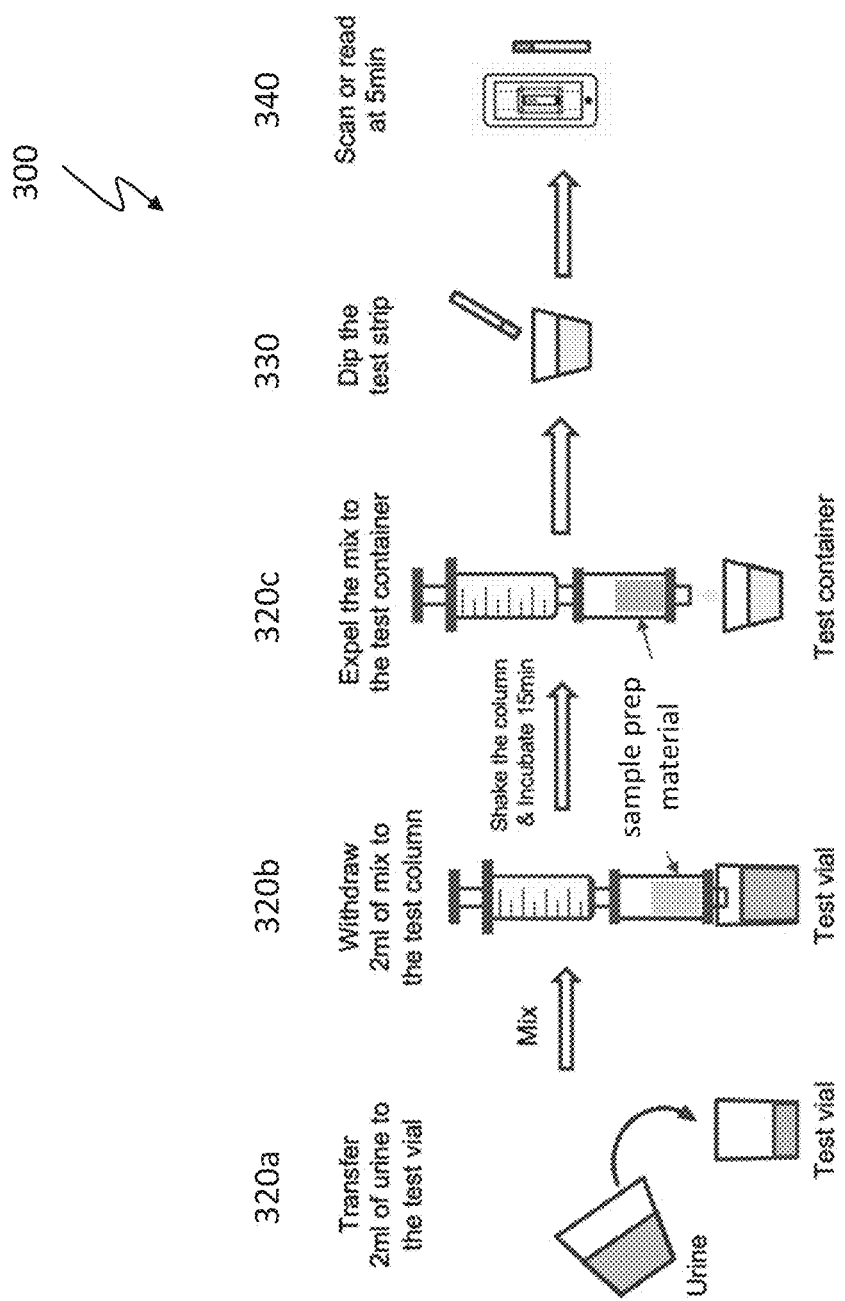
FIG. 3 depicts a schematic illustration of an example variation of a method of using a diagnostic test kit.

An example variation of using a diagnostic test kit such as that described above is illustrated in FIG. 3. As shown in FIG. 3, a method of using a diagnostic test kit may include purifying a sample at least in part by combining the sample with at least one pre-processing reagent (320a). For example, a pre-processing reagent (e.g., dry powder urease, with or without additives such as that described above) may be pre-packaged or placed in a test vial or other suitable container. A user may obtain a urine sample and transfer a designated amount (e.g., 2 ml) of urine into the container that includes the pre-processing reagent, thereby mixing the urine and the pre-processing reagent. The urine may reconstitute the pre-processing reagent into liquid, and the resulting reaction between urea and urease may sufficiently remove urea from the urine sample. In some variations, the mixture may incubate to allow for sufficient urea consumption prior to subsequent sample processing steps (e.g., passing the sample through an ion exchange resin design as described below), such as over an incubation period of between about 10 seconds and about 15 minutes. Alternatively, in some variations, the urine and reconstituted pre-processing reagent solution may be immediately further processed, such as transferred to an ion-exchange resin device, where the urea-urease reaction may continue occurring in the ion-exchange resin device described above and below.

Figure 4C:
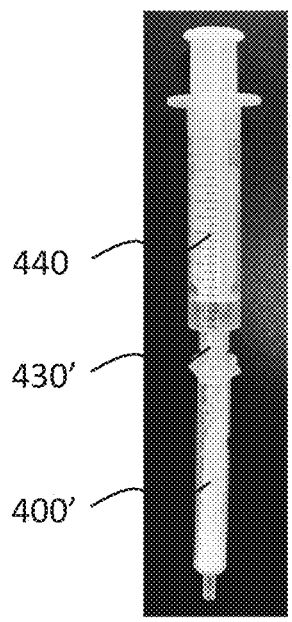
FIG. 4C depicts an example variation of an ion exchange resin device coupled to a syringe for drawing a sample into the ion exchange resin device.

The sample may be further purified at least in part by directing the sample into an ion-exchange resin device (320b) having a cation-exchange resin. The sample may be directed through the cation-exchange resin through a pressure differential, such as a negative pressure differential. For example, as shown in FIG. 4C, a syringe 440 (e.g., luer lock syringe) may be coupled via an adaptor 430 to an opening of the ion-exchange resin device 400' that is in fluidic communication with cation-exchange resin in the resin device. The syringe 440 may be actuated to draw a urine sample (e.g., a urine sample partially purified by removal of urea as described above) into the ion-exchange resin device by pulling the syringe plunger. The amount of urine that is drawn into the device can be controlled by the syringe. Once the urine sample is mixed with the cation-exchange resin, the resin can start to absorb or bind with interferent species (e.g., urobilinogen). In some variations, the ion-exchange resin device may be agitated (e.g., gently turned end-over-end, shaken, swirled, etc.) to further induce mixing between the urine sample and cation-exchange resin. The ion-exchange resin device may be placed on its side horizontally for an incubation period, and optionally agitated every few minutes to further improve mixing. After a suitable incubation period (e.g., between about 5 minutes and about 20 minutes, or between about 10 minutes and about 15 minutes), urine that contains PBG (reduced amount of interferent species) may be flushed back out of the ion-exchange rein device by pushing the syringe plunger, thereby inducing a positive pressure differential. As shown in FIG. 3, the purified urine sample may, for example, be expelled (320c) into a suitable test container. Although FIG. 3 illustrates a variation in which the urine sample is directed into the ion-exchange device via negative pressure and expelled via positive pressure, it should be understood that in some variations, the urine sample may alternatively be directed into the ion-exchange device via positive pressure and drawn back out via negative pressure (e.g., by a suitable fluid pump).

The purified sample may then be available for applying to a test strip, such as by briefly dipping a test trip into the test container containing the purified urine sample. Additionally or alternatively, one or more drops of the urine sample may be applied to the test strip. Excess urine may be blotted or otherwise removed from the test strip. The colorimetric reaction may occur over an incubation period (e.g., between about 1 minute and about 15 minutes), after which a user may obtain an image of the test strip (e.g., and also of a scan surface with a color reference chart) with a camera for analysis.

While various steps of the method may be performed manually by s user, it should be understood that in some variations at least a portion of the sample manipulation for sample purification, sample analysis, etc. may be performed in an automated or semi-automated manner with a fluidic system operable with a control system (e.g., pumps, valves, etc.).

Methods of Analyzing Diagnostic Tests

As described above, an image of a test strip may be analyzed by one or more processors to estimate an amount of an analyte of interest in a sample. In analyzing a diagnostic test, as described above, the test region of a test may be identified in the image at least in part on fiducial markers. Furthermore, calibration markers and/or other markers on the scan surface may help calibrate for camera characteristics (e.g., white balance, resolution, etc.) as described above.

In some variations, present in the scene of any colorimetric test image may be reference colors, such as in reference color blocks or other icons printed on a scan surface and depicted in the image). These reference color blocks may be located by finding their contours. Once the reference color blocks have been located, images of those color blocks may be converted to a colorspace that is best suited for the analysis of their color. Descriptive statistics representing the color blocks may be calculated and used to generate a color correction matrix, which can be applied to the entire image or just a region of interest such as the reagent pad. This color correction matrix serves to lessen the impact of unusual illuminant conditions on measurement of the reagent pad color.

In some variations, the analysis of colorimetric tests may involve semi-quantitative processes. For example, a method of analyzing a diagnostic test may include receiving an image depicting a diagnostic test and a color reference chart, where the diagnostic test includes a test region indicating a colorimetric reaction with an analyte of interest in a sample. The method may further include identifying a test region of a test and comparing a detected color value of the test region with one or more predetermined colors (e.g., color reference chart) to assess the diagnostic test result (e.g., in a semi-quantitative manner if each predetermined color in the color reference chart is associated with a range of analyte concentrations). In some variations, the color value of the reagent pad may then be translated into an analyte concentration and corresponding test result, such as with a lookup table or equation, which may be stored in memory and accessed at appropriate times. In some variations, the color-based image analysis may be similar to that described in U.S. Pat. Nos. 8,655,009 and 8,911,679, each of which is incorporated above.

Additionally or alternatively, the analysis of colorimetric tests may include quantitative processes, such as using a predictive formula. For example, in some variations, a method for analyzing a sample for an analyte of interest may include receiving an image depicting a diagnostic test region and a color reference chart, where the diagnostic test region indicates a colorimetric reaction with the analyte of interest in the sample. The method may, in some variations, further include converting a test region image portion of the image to an analytical color space (though in some variations no conversion may be required if the received image is already in the desired analytical color space). Suitable analytical color spaces may include, for example, CIELab and/or RBG, though other suitable color spaces may be appropriate.

Given the test region image portion (that is, a portion of the image that depicts the diagnostic test region, such as a reagent pad) in an analytical color space, the method may further include determining a first coordinate value and a second coordinate value characterizing the test region image portion in the analytical space. A representative pixel or group of pixels (value representative of a group of pixels) in the test region image portion may be characterized using the coordinate values. For example, a pixel in the center or centroid of a depicted reagent pad may be characterized by color space coordinates. As another example, a subset (e.g., central group) of pixels or all pixels in the reagent pad may be averaged and represented by an average set of color space coordinates.

The first coordinate value characterizing the test region image portion may correspond to a first channel in the analytical color space, and the second coordinate value characterizing the test region image portion may correspond to a second channel in the analytical color space. In some variations, additional coordinate values may be determined (e.g., a third coordinate value characterizing the test region image portion corresponding to a third channel in the analytical color space). The meaning of the coordinate values may depend on the kind of analytical color space of the converted image. For example, in some variations a received image may be converted to CIELab color space, in which the method may include determining "L", "a", and "b" coordinate values characterizing the diagnostic test region that was imaged.

The method of analyzing a sample for an analyte of interest may further include quantifying the analyte of interest in the sample based on at least one coordinate value characterizing the test region image portion and a predictive formula based on the color reference chart. For example, the quantification of the analyte of interest may be based on the first coordinate value, at least the second coordinate value, or both. In some variations, the quantification of the analyte of interest may be based on three coordinate values.

Such a predictive formula may be generated in any of various suitable manners based on the color reference chart, and during testing, the predictive formula may be accessed from one or more memory devices (e.g., in a mobile computing device executing a mobile application for test analysis, or from a cloud-based network, etc.). The color reference chart may include a plurality of reference color blocks, each of which is associated with a respective known concentration of the analyte of interest. In some variations, the predictive formula may be based on reference coordinate values (that is, in the channels of the analytical color space) characterizing each of the reference color blocks.

For example, the predictive formula may relate at least one reference coordinate value of each reference color block to the known concentration of the analyte of interest associated with each reference color block. The reference coordinate value may, for example, be for a color channel of the analytical color space. As an illustrative example, where the analytical color space is CIELab, the "a" value of each reference color block may be associated with the known analyte concentration associated with that reference color block. The "a" values of the reference color blocks may be plotted against the respective known analyte concentrations associated with the color reference blocks, and a best fit curve fitted to this plot may inform the predictive formula. As described above, this predictive formula may be stored and accessed during testing. In use during testing, the "a" value of a diagnostic test region image portion (e.g., reagent pad) may be input into the predictive formula, which returns a quantitative measurement of analyte concentration in the diagnostic test region.

As another example, the predictive formula may relate a ratio of reference coordinate values of each reference color block to the known concentration of the analyte of interest associated with each reference color block. As an illustrative example, where the analytical color space is CIELab, a ratio of "L" and "a" reference coordinate values of each reference color block may be associated with the known analyte concentration associated with that reference color block. The predictive formula may relate a ratio of "L" and "a" values may be plotted against the respective known analyte concentrations associated with the color reference block, and a best fit curve fitted to this plot may be stored and accessed during testing. In use during testing, the ratio of "L" and "a" values of a diagnostic test region image portion (e.g., reagent pad) may be input into the predictive formula, which returns a quantitative measurement of analyte concentration in the diagnostic test region.

As another example, the predictive formula may relate a distance in the analytical color space (e.g., location of coordinates of each color reference block relative to a baseline location, along a plane in the analytical color space). For example, the distance may be in a plane in the analytical color space defined by coordinates associated with at least one color channel of the analytical color space. As an illustrative example, where the analytical color space is CIELab, the distance of concern may be along the (L, a) plane, measured between each color reference block to baseline location on the (L, a) plane. These distances for the reference color blocks may be plotted against the respective known analyte concentrations associated with the color reference blocks, and a best fit curve fitted to this plot may inform the predictive formula. As described above, this predictive formula may be stored and accessed during testing. In use during testing, the similarly-determined distance (e.g., distance in the (L, a) plane relative to the baseline location) of a diagnostic test region image portion (e.g., reagent pad) may be input into the predictive formula, which returns a quantitative measurement of analyte concentration in the diagnostic test region.

The quantitative characterization of analyte concentration (e.g., as described above) allows for more objective, accurate, and precise measurements of analyte in a colorimetric test, compared to other analytical methods (e.g., semi-quantitative methods of manual readings).

After semi-quantitatively or quantitatively determining a measurement of the analyte of interest in the sample using methods such as those described above, a diagnostic test result based on the measure of the analyte of interest may be provided to a user or other suitable entity (e.g., medical professional, partner or other care supporter, etc.). For example, the analyte concentration determined through the test may be compared to a predetermined threshold for determining whether the patient supplying the tested sample may have an associated medical condition. As an illustrative example, urinary PBG levels may be compared to a first threshold to determine whether the patient is healthy (e.g., urine of health subjects typically have PBG levels below about 0.15 mg/L). Additionally or alternatively, urinary PBG levels may be compared to a second threshold to determine whether the patient is experiencing an attack of acute intermittent *porphyria*, which may be indicated by urinary PBG level that is above about 2 mg/L (and may sometimes exceed a threshold as high as about 60 mg/L).

In some variations, based on the diagnostic test result, one or more remedial or follow-up actions may be performed or suggested. For example, in response to PBG levels exceeding a predetermined threshold, the patient may be notified to seek medical attention, take certain medication for treatment, etc. As another example, in response to PBG levels exceeding a predetermined threshold, a designated medical care practitioner and/or other care supporter for the patient may be automatically contacted or certain medication may be automatically prescribed for the patient. In some variations, such actions may be performed via a mobile application executed on a mobile computing device or the like.

EXAMPLES

Example 1

Figures 10A, 10B, 10C:
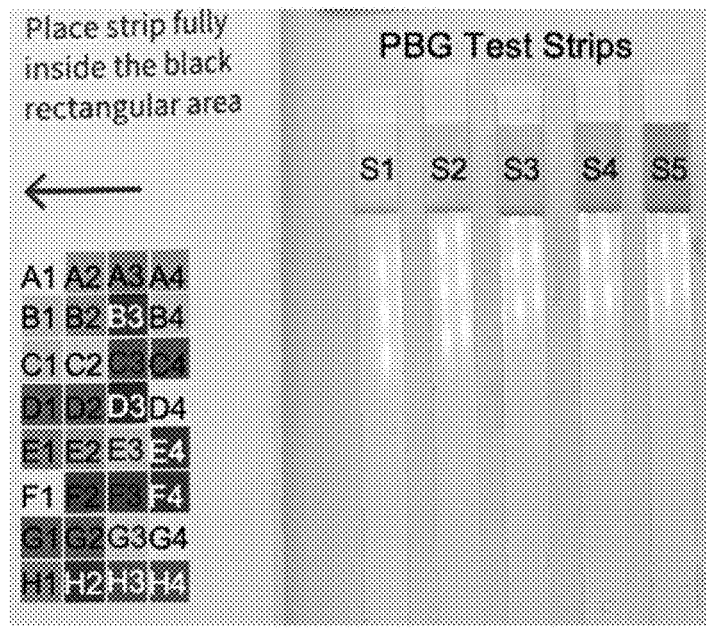
FIG. 10A depicts an example of a set of PBG test strips reacted with PBG solutions of different PBG concentrations, imaged alongside a color reference chart.
FIG. 10B summarizes Lab values for the PBG test strips.
FIG. 10C summarizes Lab values for reference color blocks in the color reference chart that most closely match the color of the PBG test strips.

FIG. 10A depicts an image of a set of PBG test strips S1-S5 and color reference chart with reference color blocks. Each of the PBG test strips was exposed to a different concentration of standard PBG solution, resulting in each PBG test strip exhibiting a different color from the colorimetric reaction. In the color reference chart, each color block is designated with a code corresponding to its relative location in the chart. Certain reference color blocks (A1, A3, B2, B4, C2, E1, E2, E3, G3, H1) in the color reference chart are close matches to colors of the PBG test strips, and hence are used to represent the PBG tests. Colors on the PBG test strips were converted to CIELab color space coordinates (FIG. 10B), as were colors in the closest-matching reference color blocks (FIG. 10C). The Lab values were used to establish descriptive statistics for use in evaluating other PBG test strips.

Figures 11A, 11B:
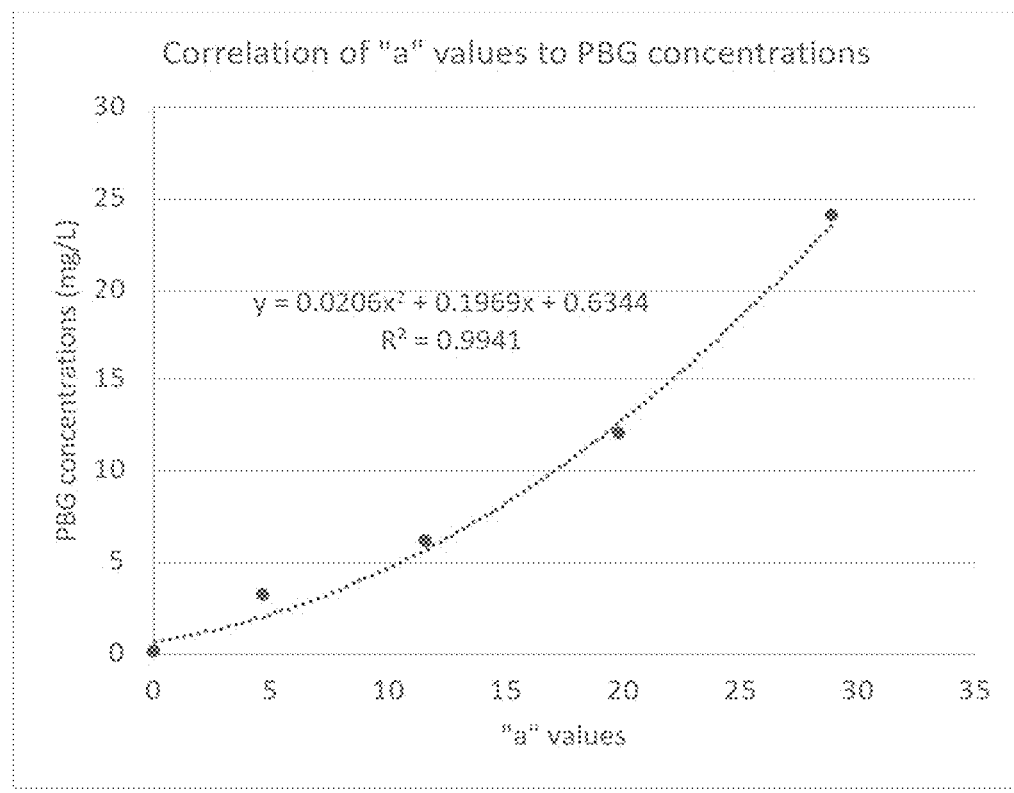
FIG. 11A summarizes "a" Lab values for some of the reference color blocks imaged in FIG. 10A and their corresponding representative known PBG concentrations.
FIG. 11B depicts a plot of data from FIG. 11A, including a fitted curve suitable for predicting PBG based on color values of PBG tests.

In one example, the "a" values from the closest-matching reference color blocks were plotted against their representative known PBG concentrations (tabulated in FIG. 11A). A correlation was observed in the resulting plot (FIG. 11B). Furthermore, a second-degree polynomial curve was fitted to the data and was used to calculate estimated PBG concentrations of the test strips S1-S5, based on the "a" color values of the imaged PBG reagent pads for test strips S1-S5 (FIG. 11C).

Figure 12A:
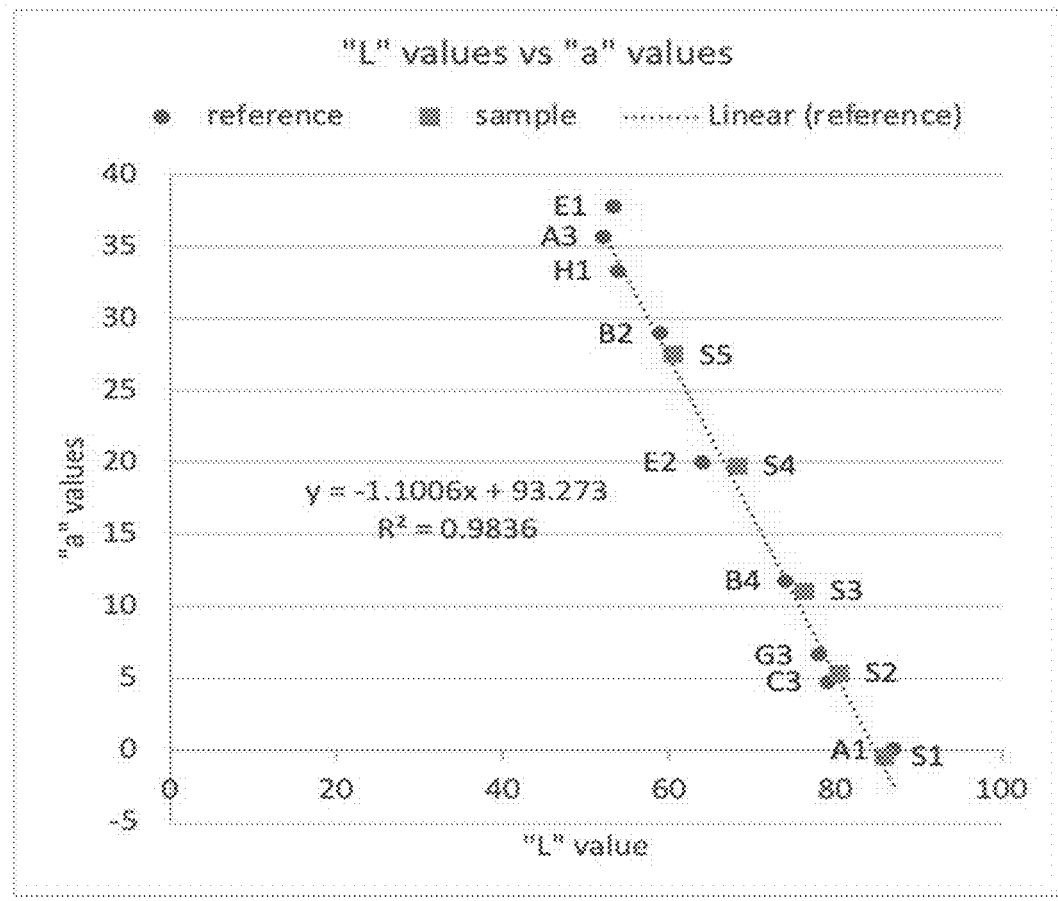
FIG. 12A depicts a plot of "L" values again "a" values for the closest-matching reference color blocks listed in FIG. 10C and the test strips shown in FIG. 10A.
Figures 12B, 12C, 12D:
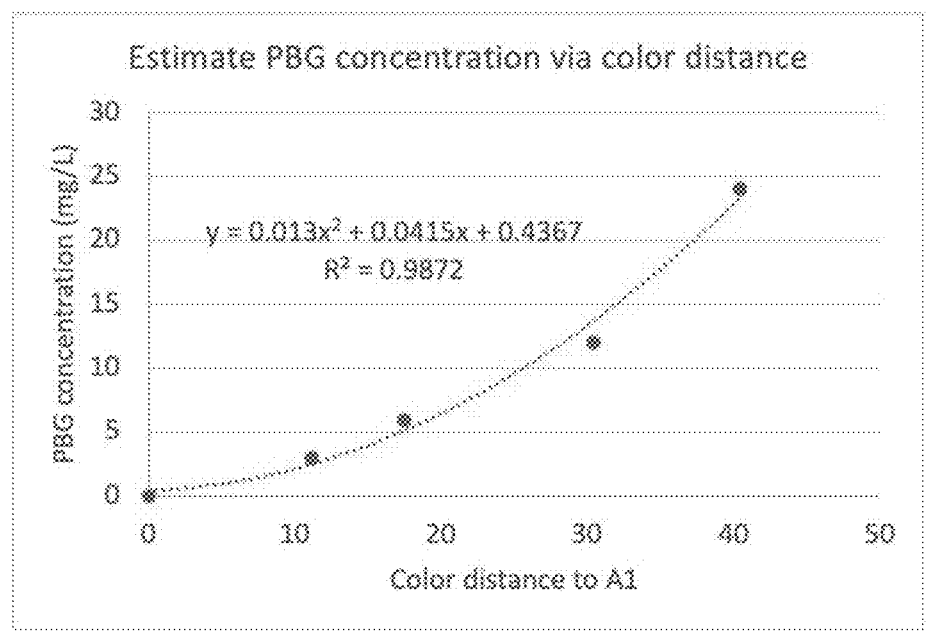
FIGS. 12B and 12C summarize and depict PBG concentration against color distance in an (L, a) plane in view of FIG. 12A, including a predictive equation suitable for predicting PBG based on color distance of PBG tests.
FIG. 12D summarizes estimated PBG concentrations for the PBG test strips shown in FIG. 10A, based on the predictive equation shown in FIG. 12C.

In another example, the "L" values were plotted against the "a" values, which revealed a linear relationship (FIG. 12A) consistent with the "L" and "a" values for the test strips S1-S5 and their associated reference color blocks. This linear relationship may be characterized with a fitted curve to serve as one type of PBG predictive formula. Next, the color block A1, which represents the PBG concentration at 0 mg/L, was used as a baseline to calculate the distance in the (L, a) plane from other reference color blocks to the baseline. These distances, as well as representative known PBG concentrations, for the reference color blocks are shown in FIG. 12B. The distance values were plotted against PBG concentrations that are correlated to the closest-matching reference color blocks (FIG. 12C). A 2nd order of polynomial curve fit the presented data to serve as a PBG predictive formula. Finally, to estimate the PBG concentrations of the test strips S1-S5, the distance in the (L, a) plane from the test strips' color to color block A1 was used as input for the PBG predictive equation. These distances, entered into the PBG predictive formula, were used to obtain the estimated PBG concentrations of the test strips S1-S5 (FIG. 12D).

Example 2

Figure 13:
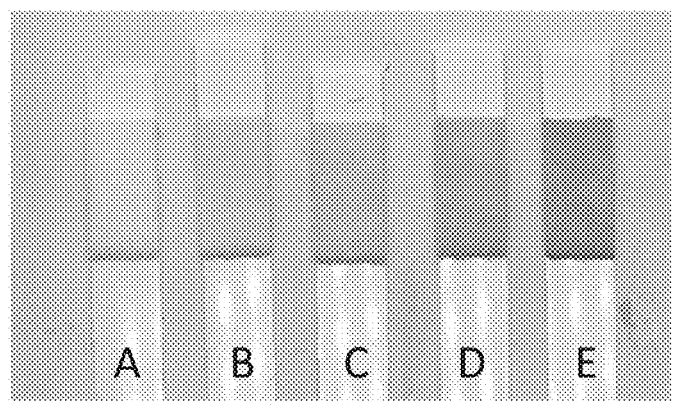

FIG. 13 illustrates a set of PBG test strips A-E to which standard PBG solutions were applied. The PBG reactive reagents impregnated on the PBG test strips reacted with PBG and turned the test strips A-E into varying shades of a magenta color. The intensity of the magenta color was proportional to the PBG concentrations. For example, the test strip B that reacted with a 3 mg/L PBG solution was a less intense shade of magenta than the test strip E that reacted with a 24 mg/L PBG solution, thereby confirming that the PBG test strips were able to exhibit a color change that was correlated to PBG concentration.

Example 3

Figure 14:
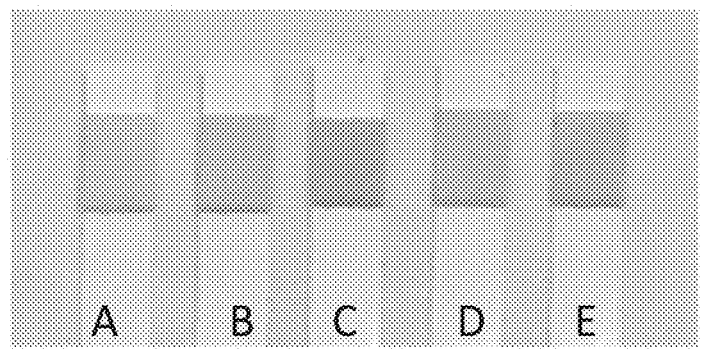

FIG. 14 illustrates a set of PBG test strips A-E that illustrate the effect of using pre-processing reagents to remove interferent urea from urine samples. Test strips A, B, and C were reacted with urine that was not pre-processed with a pre-processing reagent to remove interferent urea (i.e., unprocessed urine). Specifically, test strip A was reacted with unprocessed urine with no PBG, test strip B was reacted with unprocessed urine in the presence of 6 mg/L PBG, and test strip C was reacted with unprocessed urine in the presence of 24 mg/L PBG. None of the test strips A-C exhibited a characteristic magenta color ideally used to indicate PBG concentration for the PBG test.

Test strips D and E were reacted with urine that was pre-processed with a pre-processing reagent to remove interference urea (i.e., processed urine). Specifically, test strip D was reacted with processed urine in the presence of 6 mg/L PBG, and test strip E was reacted with processed urine in the presence of 24 mg/L PBG. Test strips D and E exhibited characteristic shades of magenta color for indicating PBG concentration for the PBG test. Furthermore, the test results of unprocessed urine and processed urine with identical PBG levels (e.g., test strips B and D, and test strips C and E) were markedly distinct, thereby illustrating the difference in visual results of the PBG test that is caused by failing to remove interferent urea from the urine sample prior to performing a PBG test.

Example 4

FIG. 15 illustrates a set of PBG test strips A-H that illustrate the effect of using pre-processing reagents to remove other interferents from urine samples. Test strips A, C, E, and G were reacted with urine that was not pre-processed with a pre-processing reagent to remove interferent urea (i.e., unprocessed urine). Other test strips, test strips B, D, F, and H, were reacted with urine that was pre-processed with such a pre-processing reagent that removed interferent urea, but not urobilinogen. Test strips A and B were reacted with control urine samples, while test strips C and D were reacted with urine including PBG, test strips E and F were reacted with urine including urobilinogen, and test strips G and H were reacted with urine including bilirubin.

As shown in FIG. 15, the presence of urea in each of the unprocessed urine caused the reagent pad to turn yellow when the unprocessed urine was applied to test strips A, C, E, and G, confirming that presence of urea in the urine sample interferes with the result of the PBG test.

The color difference between test strips C and D (reacted with unprocessed PBG urine and processed PBG urine, respectively) confirms that urea removal through pre-processing leads to a more accurate PBG test result (test strip D). However, even though urea was removed in the pre-processed urine that was applied to test strip F (processed URO urine) and test strip H (processed BIL urine), the reagent pads of these test strips exhibit magenta and beige colors indicating that urobilinogen and bilirubin can still react with the PBG reactive reagent on the PBG test strips. Accordingly, this example suggests the importance of removing urobilinogen and bilirubin as interferent substances for a PBG test (e.g., with an ion-exchange resin device such as that described herein).

Example 5

FIG. 16 illustrates a set of PBG test strips A-H that indicate the effect of using an ion-exchange resin device to remove interferent urobilinogen from urine samples. The ion-exchange resin device used in relation to FIG. 16 was a cation-exchange resin device that adsorbed urobilinogen from the urine sample and thus removed it from reacting with the PBG test strip. Test strips A-D were reacted with urine having 100 uM PBG but not urobilinogen, and that was processed with varying amounts of ion-exchange resin that was selected to remove interference urobilinogen and hence was superfluous for test strips A-D, which exhibited characteristic shades of magenta for PBG tests. Test strips E-H were reacted with urine having 100 uM urobilinogen, and that was processed with varying amounts of ion-exchange resin with varying degrees of success in remove a sufficient amount of urobilinogen. For example, test strip H appears white, which is indicative of an absence of a reaction between the PBG reactive reagent and both PBG and urobilinogen, indicating that the urobilinogen was largely removed from the urine sample.

Example 6

FIG. 17 illustrates a set of PBG test strips A-J that indicate the effect of using an ion-exchange resin device to remove other interferents (bilirubin, biliverdin, ALA, and Indican). For example, test strip A was reacted with urine having 100 uM PBG that was neither pre-treated with urease nor passed through the ion-exchange resin device (i.e., unprocessed urine), while test strip B was reacted with the same urine except the urine was pre-treated with urease and further processed by passing through the ion-exchange resin device. The urine that reacted with test strip B had interferents successfully removed by the urease and ion-exchange resin device, as indicated by the characteristic magenta color of test strip B. As another example, test strips C and D were reacted with urine having 100 uM bilirubin, except that for test strip D the urine's bilirubin was successfully removed by the urease and the ion-exchange resin device, as shown by the white-colored test strip D. Similarly, test strips E and F illustrate the successful removal of urea and biliverdin from urine by urease and an ion-exchange resin device, test strips G and H illustrate the successful removal of urea and ALA by urease and an ion-exchange resin device, and test strips I and J illustrate the successful removal of urea and Indican by urease and an ion-exchange resin device.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A kit for quantification of porphobilinogen (PBG) in a urine sample, the kit comprising:
   a) diagnostic test strip comprising:
      a substrate impregnated with a dried solution comprising an acid, a reagent reactive with PBG, and one or more stabilizers;
   b) a pre-processing reagent comprising urease,
      wherein the amount of pre-processing reagent is sufficient to remove urea such that a 2 ml urine sample contacted with pre-processing reagent for a period of 10 seconds to 15 minutes will contain an amount of urea that is undetectable by the test strip; and
   c) a cation-exchange resin device comprising a vessel and a cation-exchange resin arranged in the vessel,
      wherein the cation-exchange resin binds to urobilinogen at an affinity greater than it binds to PBG, such that a urine sample of 2 ml contacted with the cation-exchange resin in the vessel for a period 5 to 20 minutes will contain an amount of urobilinogen that is undetectable by the test strip but will contain an amount of PBG detectable by the test strip.

2. The kit of claim 1, wherein the reagent reactive with porphobilinogen comprises a benzaldehyde derivative.

3. The kit of claim 2, wherein the reagent reactive with porphobilinogen comprises one or more selected from the group consisting of para-Dimethylaminobenzaldehyde, para-Diethylaminobenzaldehyde, 4-(N,N-bis-(2-cyanoethyl)-amino)-benzaldehyde, 4-(N,N-bis-(2-cyanoethyl)-amino)-benzaldehyde, 4-(4-Methylpiperazinyl)benzaldehyde 4-[(2-Cyanoethyl)methylamino]benzaldehyde N-Methyl-N-(2-hydroxyethyl)-4-aminobenzaldehyde, 4-[Bis[2-(acetyloxy)ethyl]amino]benzaldehyde, and 4-(Boc-amino)benzaldehyde.

4. The kit test strip of claim 1, wherein the reagent reactive with porphobilinogen comprises an Azo dye.

5. The kit tip of claim 1, wherein the acid comprises one or more selected from the group consisting of: oxalic acid, maleic acid, and a salicylic-derivative acid.

6. The kit of claim 1, wherein the one or more stabilizers comprises one or more selected from the group consisting of EDTA, caffeine, borate salt, sodium benzoate, and sodium acetate.

7. The kit of claim 1, wherein the dried solution further comprises one or more additives configured to increase bonding of the reagent to the substrate.

8. The kit of claim 7, wherein the one or more additives comprises one or more selected from the group consisting of polyvinyl alcohol, polyvinyl pyrrolidone, copolymers of polyvinyl pyrrolidone and polyvinyl acetate, polyglycols, methyl vinyl ether, and maleic anhydride.

9. The kit of claim 1, wherein the substrate comprises a fiber paper.

10. The kit of claim 1, wherein the substrate is laminated onto a backing.

11. The kit of claim 10, wherein the backing comprises a flexible polymer.

12. The kit of claim 1, wherein the urease is dry powder urease.

13. The kit of claim 1, wherein the cation-exchange resin comprises one or more resins selected from the group consisting of: 1,4-bis(ethenyl)benzene; (4-ethenylphenyl)-trimethylazanium; styrene; chloride, 3-[(3-chlorophenyl)sulfonylamino]benzoic acid, and 1,2-bis(ethenyl)benzene; 1-ethenyl-2-ethylbenzene; styrene.

14. The kit of claim 1, wherein the cation-exchange resin device is configured to couple to a fluid actuating device.

* * * * *

UNITED STATES PATENT AND TRADEMARK OFFICE
CERTIFICATE OF CORRECTION

PATENT NO. : 12,235,217 B2
APPLICATION NO. : 17/098236
DATED : February 25, 2025
INVENTOR(S) : Yunyuan Vivian Wang et al.

Page 1 of 1

It is certified that error appears in the above-identified patent and that said Letters Patent is hereby corrected as shown below:

In the Claims

At Column 22, Line 66, in Claim 4, delete "The kit test strip of" and add -- The kit of --.

At Column 23, Line 1, in Claim 5, delete "The kit tip of" and add -- The kit of --.

Signed and Sealed this
Fifteenth Day of April, 2025

Coke Morgan Stewart
*Acting Director of the United States Patent and Trademark Office*